US011446333B2

(12) United States Patent
Yi et al.

(10) Patent No.: US 11,446,333 B2
(45) Date of Patent: Sep. 20, 2022

(54) USE OF COMPOSITION COMPRISING STEM CELL-DERIVED EXOSOME AS EFFECTIVE INGREDIENT FOR SUPPRESSION OR ALLEVIATION OF PRURITUS

(71) Applicant: ExoCoBio Inc., Seoul (KR)

(72) Inventors: Yong Weon Yi, Seoul (KR); Byong Seung Cho, Gunpo-si (KR)

(73) Assignee: ExoCoBio Inc., Seoul (KR)

( * ) Notice: Subject to any disclaimer, the term of this patent is extended or adjusted under 35 U.S.C. 154(b) by 381 days.

(21) Appl. No.: 16/727,173

(22) Filed: Dec. 26, 2019

(65) Prior Publication Data

US 2020/0121722 A1    Apr. 23, 2020

Related U.S. Application Data

(63) Continuation of application No. PCT/KR2018/007369, filed on Jun. 28, 2018.

(30) Foreign Application Priority Data

Jun. 30, 2017 (KR) .................. 10-2017-0083508
Jun. 2, 2018  (KR) .................. 10-2018-0063921

(51) Int. Cl.
*A61K 35/28* (2015.01)
*A61P 17/04* (2006.01)
*A61K 9/00* (2006.01)
*A61K 47/36* (2006.01)
*A61N 1/04* (2006.01)
*A61N 1/32* (2006.01)

(52) U.S. Cl.
CPC ............ *A61K 35/28* (2013.01); *A61K 9/0009* (2013.01); *A61K 47/36* (2013.01); *A61N 1/0428* (2013.01); *A61N 1/325* (2013.01); *A61P 17/04* (2018.01)

(58) Field of Classification Search
None
See application file for complete search history.

(56) References Cited

U.S. PATENT DOCUMENTS

2015/0125950 A1*  5/2015  Lim .................... C12N 5/0668
                                                 435/325
2019/0231694 A1*  8/2019  Lim ....................... A61K 47/26

FOREIGN PATENT DOCUMENTS

| KR | 10-2012-0087625 A | 8/2012 |
|---|---|---|
| KR | 10-2015-0088374 A | 8/2015 |
| KR | 10-2016-0026234 A | 3/2016 |
| KR | 10-2016-0033555 A | 3/2016 |
| KR | 10-1661353 B1 | 10/2016 |
| KR | 10-1686064 B1 | 12/2016 |
| KR | 10-2017-0044999 A | 4/2017 |
| WO | 2009/105044 A1 | 8/2009 |
| WO | 2015/179227 A1 | 11/2015 |

OTHER PUBLICATIONS

Cho et al. (2018) Stem Cell Research & Therapy 9: 187 (5 pages). (Year: 2018).*
Johnsen et al. (2016) Cytotechnology 68: 2125-2138. (Year: 2016).*
Wilson et al. (2013) Cell 155, 285-295. (Year: 2013).*
Priya et al. (2005) Expert Opinion on Drug Delivery 3: 1: 127-138. (Year: 2005).*
Byong Seung Cho et al., "Exosomes derived from human adipose tissue-derived mesenchymal stem cells alleviate atopic dermatitis", Stem Cell Research & Therapy, Jul. 11, 2018, vol. 9, No. 1, pp. 1-5 (5 pages total).
Steffi Bosch, et al., "Trehalose prevents aggregation of exosomes and cryodamage", Scientific Reports, 2016, pp. 1-11, vol. 6, Article No. 36162.
Sarah R. Wilson, et al., "The Epithelial Cell-Derived Atopic Dermatitis Cytokine TSLP Activates Neurons to Induce Itch", Cell, Oct. 10, 2013, pp. 285-295, vol. 155.
International Search Report for PCT/KR2018/007369 dated Mar. 29, 2019 [PCT/ISA/210].
Written Opinion for PCT/KR2018/007369 dated Mar. 29, 2019 [PCT/ISA/237].
Written Opinion of International Preliminary Examination Authority for PCT/KR2018/007369 dated Mar. 29, 2019 [PCT/ISA/408].
Hae-Jin Lee et al., "The Effect of Adipose-Derived Stem Cell-Cultured Media on Oxazolone Treated Atopic Dermatitis-Like Murine Model", Ann Dermatol, ADSC Media on Atopic Dermatitis Model, 2012, vol. 24, No. 2, pp. 181-188 (8 pages).

* cited by examiner

*Primary Examiner* — Russell G Fiebig
(74) *Attorney, Agent, or Firm* — Sughrue Mion, PLLC

(57) ABSTRACT

The present invention provides a composition for preventing, suppressing, alleviating, ameliorating or treating pruritus comprising stem cell-derived exosomes as an active ingredient. The composition of the present invention is able to act against pruritus-inducing multiple cytokine targets, for example, IL-4, IL-31 and TSLP, and thus is able to be widely applied against pruritus caused by various factors and is able to effectively suppress and alleviate pruritus. In addition, when the composition of the present invention is applied directly to human skin, it is able to remarkably ameliorate pruritus-associated clinical scores, erythema and the like. Thus, the composition of the present invention is able to be used as a pharmaceutical composition, a skin external preparation and a cosmetic composition for preventing, suppressing, alleviating, ameliorating or treating pruritus.

18 Claims, 29 Drawing Sheets
(4 of 29 Drawing Sheet(s) Filed in Color)
Specification includes a Sequence Listing.

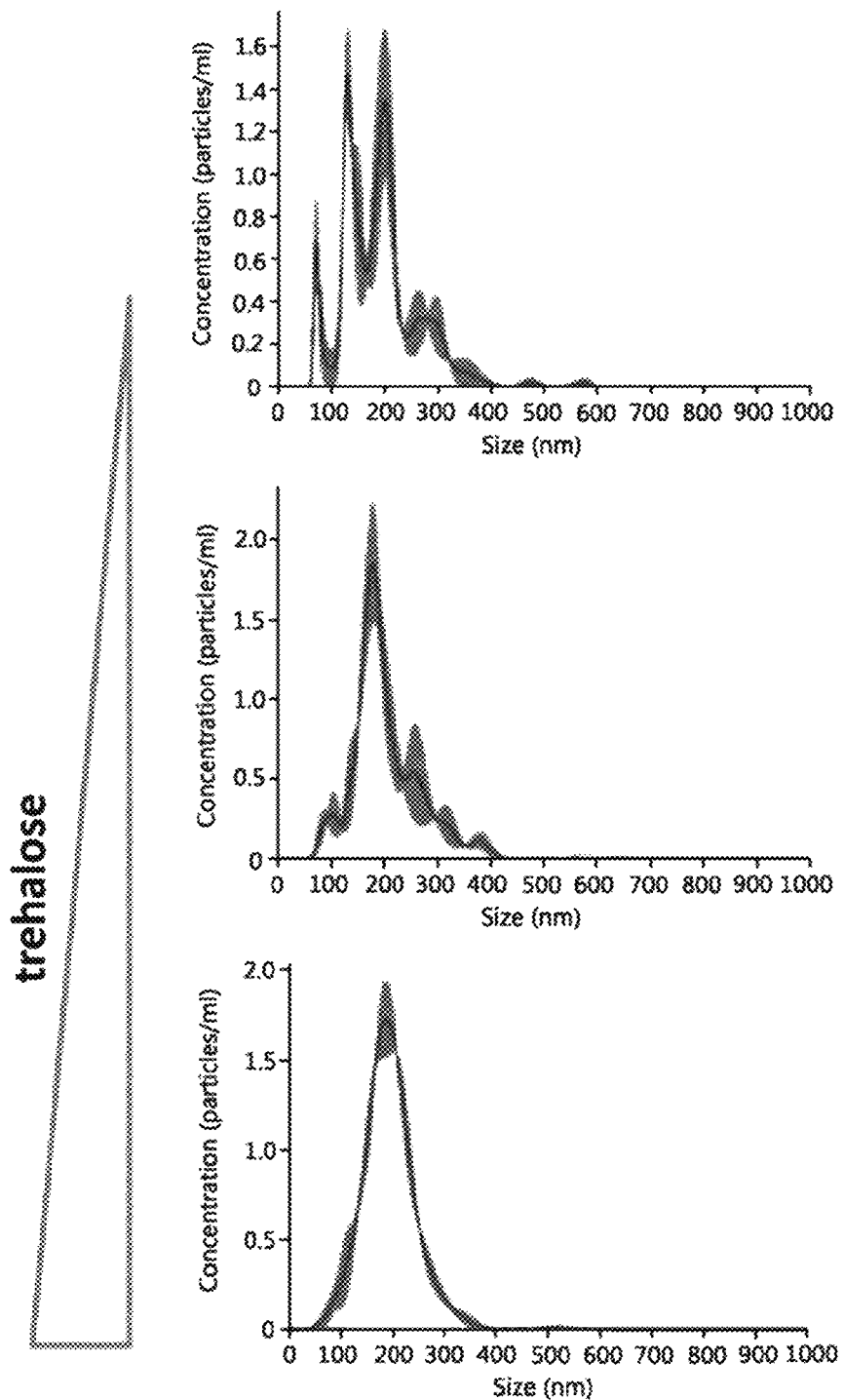

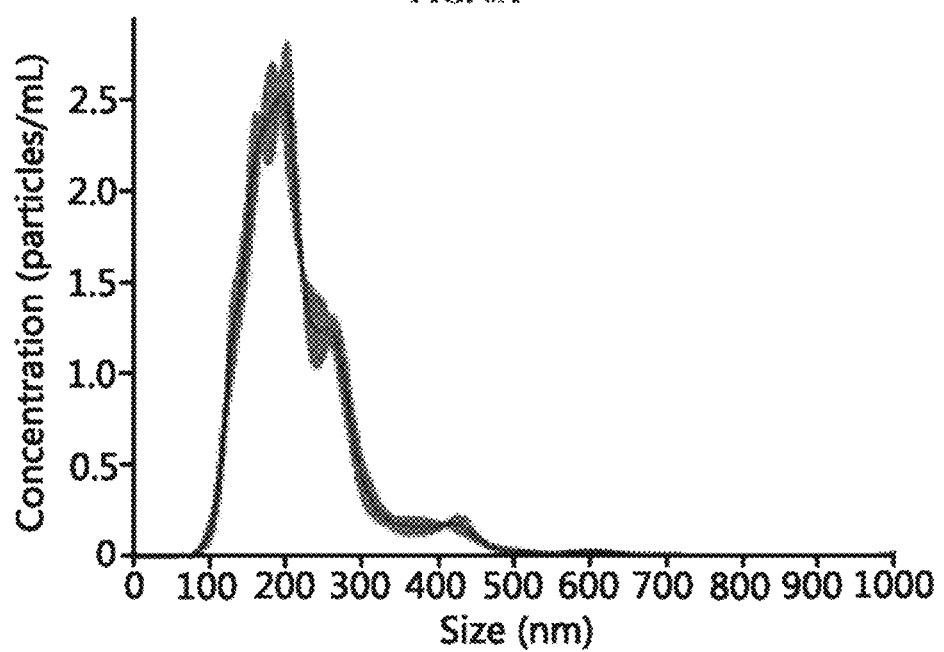

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: IL-4 forward primer

<400> SEQUENCE: 1
acaggagaag ggacgccat                                                19
```

<210> SEQ ID NO 2
<211> LENGTH: 21
<212> TYPE: DNA
<213> ORGANISM: Artificial Sequence
<220> FEATURE:
<223> OTHER INFORMATION: IL-4 reverse primer

<400> SEQUENCE: 2
gaagccctac agacgagctc a                                              21

<210> SEQ ID NO 3
<211> LENGTH: 20
<212> TYPE: DNA
<213> ORGANISM: Artificial Sequence
<220> FEATURE:
<223> OTHER INFORMATION: IL-31 forward primer

<400> SEQUENCE: 3
cacacaggaa caacgaagcc                                                20

<210> SEQ ID NO 4
<211> LENGTH: 19
<212> TYPE: DNA
<213> ORGANISM: Artificial Sequence
<220> FEATURE:
<223> OTHER INFORMATION: IL-31 reverse primer

<400> SEQUENCE: 4
cgatattggg gcaccgaag                                                 19

<210> SEQ ID NO 5
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 5
catggccttc cgtgttccta                                                20

<210> SEQ ID NO 6
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 6
cctgcttcac caccttcttg at                                             22

<210> SEQ ID NO 7
<211> LENGTH: 21
<212> TYPE: DNA
<213> ORGANISM: Artificial Sequence
<220> FEATURE:
<223> OTHER INFORMATION: TSLP forward primer

<400> SEQUENCE: 7
gctatctggt gcccaggcta t                                              21

<210> SEQ ID NO 8
<211> LENGTH: 21
<212> TYPE: DNA
<213> ORGANISM: Artificial Sequence
<220> FEATURE:
<223> OTHER INFORMATION: TSLP reverse primer

```
<400> SEQUENCE: 8
cgacgccaca atccttgtaa t                                              21

<210> SEQ ID NO 9
<211> LENGTH: 20
<212> TYPE: DNA
<213> ORGANISM: Artificial Sequence
<220> FEATURE:
<223> OTHER INFORMATION: beta-actin forward primer

<400> SEQUENCE: 9
ggccatctct tgctcgaagt                                                20

<210> SEQ ID NO 10
<211> LENGTH: 20
<212> TYPE: DNA
<213> ORGANISM: Artificial Sequence
<220> FEATURE:
<223> OTHER INFORMATION: beta-actin reverse primer

<400> SEQUENCE: 10
gacaccttca acacccagc                                                 20
```

USE OF COMPOSITION COMPRISING STEM CELL-DERIVED EXOSOME AS EFFECTIVE INGREDIENT FOR SUPPRESSION OR ALLEVIATION OF PRURITUS

CROSS REFERENCE

This application is a Bypass Continuation of International Application No. PCT/KR2018/007369 filed Jun. 28, 2018, claiming priority based on Korean Patent Application No. 10-2017-0083508 filed Jun. 30, 2017 and Korean Patent Application No. 10-2018-0063921 filed Jun. 2, 2018, the entire contents of which are incorporated herein by reference.

TECHNICAL FIELD

The present invention relates to the use of a composition including stem cell-derived exosomes as an active ingredient for preventing, suppressing, alleviating, ameliorating or treating pruritus.

Moreover, the present invention relates to a pharmaceutical composition, skin external preparation and cosmetic composition including stem cell-derived exosomes for preventing, suppressing, alleviating, ameliorating or treating pruritus.

In addition, the present invention relates to a clinically and commercially relevant technology capable of obtaining a large amount of stem cell-derived exosomes which are clinically applicable for the prevention, suppression, alleviation, amelioration and treatment of pruritus and have high purity and a uniform particle size distribution, in which the technology can provide a composition which includes as an active ingredient, the obtained stem cell-derived exosomes having excellent functional activity, in large amounts at low costs.

BACKGROUND ART

Itching or pruritus is a symptom characterized in that itching itself is regarded as a disease. Pruritus is an unpleasant symptom that appears in various conditions and disorders. Particularly, it is a symptom that can be often found in skin diseases and systemic diseases. Pruritus is a sensation that often occurs in most skin diseases with pain, and is clinically defined as an unpleasant sensation that provokes the desire to scratch or rub the skin.

Scratching the skin due to pruritus causes wounds and leads to bacterial infection and inflammation. Due to such bacterial infection and inflammation, immune cells such as T-cells and macrophages are activated and various cytokines are secreted, thus further exacerbating pruritus. Patients with pruritus scratch the affected area consciously or unconsciously. When the affected area is severely scratched or rubbed, the scratches may remain severe, or various side effects such as erythema, cracks, ulcer, urticaria or pigmentation may appear.

The known causes of pruritus include dermatological causes, systemic causes, neuropathic causes and psychogenic causes. In addition, pruritus may be caused or worsened by various stimuli, including physical, mechanical, chemical or biological factors. For example, pruritus may be caused by environmental triggers, including climate, particulate matters, detergents, fungal or bacterial skin infections, insect bites and body invaders; diseases, including diabetes, uremia, biliary atresia, malignant tumors, liver diseases, renal failure, kidney dialysis, gout, thyroid diseases, blood disorders, iron deficiency, delusional parasitosis, polycythemia rubra vera, cholestasis and Hodgkin's disease; pregnancy, pharmaceutical or psychogenic factors. It is thought that the sensation of itching occurs because an itching stimulus acts on the multi-stimulation responsive nerve endings (itching receptors) present at the epidermal-dermis interface and the resulting impulse reaches the spinal thalamus, thalamus, and cerebral cortex in order (Miyachi Yoshiki, Approach to the Treatment of Skin Pruritus, p.22, 1996, Sendan Igakusha).

Pruritus is classified by causes into: 1) paroxysmal pruritus that occurs paroxysmally; 2) skin pruritus including winter itch, anal itching (pruritus ani), pruritus vulvae (itchy vulva), Jock itch (tinea cruris), aquagenic pruritus, and scalp pruritus; 3) pruritus associated with internal diseases, including cholestatic pruritus, chronic renal failure, malignant tumors, iron deficiency anemia, polycythemia rubra vera, hyperthyroidism, hypothyroidism, diabetes, and acquired immunodeficiency syndrome; 4) pruritus associated with mental skin disorders, including lichen simplex chronicus, prurigo, trichotillomania, nervous scratches, behavioral disorders affecting the skin, and delusional parasitosis; and 5) nasal pruritus and itchy throat associated with flu or the like, ocular pruritus associated with eye diseases such as conjunctivitis, oral pruritus associated with dental diseases, etc.

According to research results reported to date, it is known that pruritus mediators cause pruritus in various skin diseases. Specifically, it is known that various cytokines (IL-4, IL-13, IL-31, etc.) and histamines secreted from immune cells (T cells, macrophages, etc.) cause pruritus. In addition, in recent years, it has been known that TSLP (thymic stromal lymphopoietin) is associated with the severity of dermatitis and causes itching symptoms (Wilson S R et al., The epithelial cell-derived atopic dermatitis cytokine TSLP activates neurons to induce itch. Cell. 2013; 155(2):285-95).

According to the National Health Information Portal for Medical Information (http://health.mw.go.kr), it is known that mediators that induce pruritus include histamines, serotonin, prostaglandin E, tachykinin, cytokines, protease, opioid peptides, platelet-activating factors, etc.

Among the pruritus-inducing substances, cytokines are low-molecular-weight proteins produced by all types of eukaryotic cells, interact with cell surface receptors, and include interleukins, chemokines, interferons, and the like. Among them, IL-4, IL-13, IL-31, TSLP and the like are known as representative cytokines that induce pruritus.

As treatments for pruritus, which have been reported to date, there are various treatments, including antihistamines, steroids, antibiotics, antiviral agents, antifungal agents, anesthetics, probiotics, immunosuppressants, phototherapy, and the like. However, these treatments have problems that they have temporal or limited therapeutic effects and show specificity depending on the kind of pruritus. In addition, adrenocortical hormones and corticosteroids have a problem that they should be used only in acute or severe cases for a short period of time due to their side effects.

In view of these problems, studies have been actively conducted to suppress or alleviate pruritus using natural substances. In the case of compositions for suppressing or alleviating pruritus, which are based on these natural substances, the content of an active ingredient in the natural extract is low, and hence a large amount of the natural extract needs to be used to obtain the effect of suppressing or alleviating pruritus. In the majority of cases, the fact that these compositions are based on natural substances has been emphasized in marketing, but there is a need for more scientific research on the practical effects of natural substances on the suppression or alleviation of pruritus.

Meanwhile, methods for ameliorating or treating skin conditions or diseases using stem cells have been proposed. Embryonic stem cells or fetal tissue-derived stem cells have an excellent ability to differentiate and excellent regeneration and treatment abilities, and cause less rejection, but these stem cells are not clinically applicable due to ethical issues and potential risk of tumor formation. As an alternative thereto, methods for ameliorating or treating skin conditions or diseases using adult stem cells have been proposed. However, the use of allogeneic adult stem cells, not patient's autologous adult stem cells, may pose a risk of causing graft-versus-host disease. When autologous adult stem cells are used for treatment, a problem arises that a process of culturing adult stem cells isolated from a patient is necessary, which is complicated and costly.

In recent years, in view of the above-described problems of stem cells, attempts have been made to ameliorate or treat skin conditions or diseases using conditioned media obtained by culturing adult stem cells. However, the conditioned media of adult stem cells contain not only various proteins, cytokines, and growth factors secreted by adult stem cells, but also components such as waste products secreted during growth of the cells, antibiotics added to prevent contamination, animal-derived serum and the like. Thus, when the conditioned media are used on the skin, the skin is highly likely to be exposed to various risks.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The extracellular vesicle is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome's cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

However, although various studies have been conducted which suggest a possibility for the treatment of some diseases using exosomes, more detailed clinical and non-clinical studies are required, and in particular, there is a need to develop a technology using exosomes, which can be applied for the treatment of a variety of diseases, by scientifically identifying a variety of targets on which exosomes act.

The present inventors have made efforts to develop a composition for suppressing and alleviating pruritus, which is superior to and safer than conventional therapeutic agents known with respect to pruritus. Accordingly, the present inventors have conducted extensive studies on the novel use of exosomes derived from stem cells, and as a result, have found that exosomes isolated from the conditioned media of stem cells can solve the safety problems of the stem cells themselves or the conditioned media as described above, and is effective for the prevention, suppression, alleviation, amelioration or treatment of pruritus, thereby completing the present invention.

Meanwhile, it is to be understood that the matters described as the background art are intended merely to aid in the understanding of the background of the present invention and are not admitted as prior art against the present invention.

SUMMARY OF INVENTION

It is an object of the present invention to provide the use of a composition including stem cell-derived exosomes as an active ingredient for preventing, suppressing, alleviating, ameliorating or treating pruritus.

Another object of the present invention is to provide a pharmaceutical composition, skin external preparation and cosmetic composition including stem cell-derived exosomes for preventing, suppressing, alleviating, ameliorating or treating pruritus.

Still another object of the present invention is to obtain a large amount of stem cell-derived exosomes having high purity and a uniform particle size distribution and to provide a composition including as an active ingredient, the obtained stem cell-derived exosomes having excellent functional activity.

Yet another object of the present invention is to provide a method of preventing, suppressing, alleviating, ameliorating or treating pruritus using the composition.

Further yet another object of the present invention is to provide a cosmetic method for regulating mammalian skin conditions, except for treatment purposes, by using the composition.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

To achieve the above objects, the present invention provides a composition for preventing, suppressing, alleviating, ameliorating or treating pruritus including stem cell-derived exosomes as an active ingredient.

The present invention also provides a clinically and commercially relevant novel technology capable of obtaining a large amount of stem cell-derived exosomes which are clinically applicable for the prevention, suppression, alleviation, amelioration and treatment of pruritus and have high purity and a uniform particle size distribution, in which the technology can provide a composition which includes as an active ingredient, the obtained stem cell-derived exosomes having excellent functional activity, in large amounts at low costs.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosomes' cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

As used herein, the term "itching" or "pruritus" is not particularly limited. Examples of pruritus include paroxysmal pruritus, winter itch, anal itching (pruritus ani), pruritus vulvae (itchy vulva), Jock itch (tinea cruris), aquagenic pruritus, scalp pruritus, nasal pruritus, itchy throat, oral pruritus, and eye pruritus; pruritus associated with internal diseases, including cholestatic pruritus, chronic renal failure, malignant tumors, iron deficiency anemia, polycythemia rubra vera, hyperthyroidism, hypothyroidism, diabetes, and acquired immunodeficiency syndrome; and pruritus associated with mental skin disorders, including lichen simplex chronicus, prurigo, trichotillomania, nervous scratches, behavioral disorders affecting the skin, and delusional parasitosis. However, it is to be understood that pruritus of various causes other than the above-listed pruritus is not excluded in the present invention. For example, the present invention may include all known pruritus in the art, for example pruritus of dermatological causes, systemic causes, neuropathic causes and psychogenic causes.

As used herein, the term "iontophoresis" refers to a method of flowing a microcurrent through a skin to which an active ingredient has been applied, generating a potential difference thereby and changing the electrical environment of the skin, and thus allowing an ionized active ingredient to penetrate the skin by electrical repulsion. Examples of iontophoresis that is used in one embodiment of the present invention include: a method of introducing a microcurrent into a skin by allowing the microcurrent to flow from an external power source into an electrode patch on the skin, the microcurrent generated by the external power source; a method of introducing a microcurrent into a skin, the microcurrent generated by a battery provided in an electrode patch on the skin; and a method of introducing a microcurrent into a skin through a patch on the skin provided with a reverse electrodialysis device, the microcurrent generated by the concentration difference between high concentration electrolyte solution and low concentration electrolyte solution in the reverse electrodialysis device. However, the present invention is not limited thereto, and various types of iontophoresis may, of course, be used.

Meanwhile, the limited effects of stem cell-derived exosomes on wrinkle amelioration and skin regeneration were reported. However, skin regeneration using exosomes in this conventional art is not directed to the prevention, suppression, alleviation, amelioration or treatment of pruritus, but is directed to ameliorating wrinkles or restoring skin elasticity by regenerating skin tissue. In addition, there have been attempts to use stem cells, conditioned media of stem cells, etc. to regenerate the dermal layer of skin for healing wounds, and to regenerate skin tissue for improving skin elasticity. However, it was never known that the use of exosomes isolated and purified from the conditioned media of stem cells is effective for "the prevention, suppression, alleviation, amelioration or treatment of pruritus" defined as described above.

Until now, a therapeutic agent has not been developed, which makes it possible to clinically apply exosomes for the prevention, suppression, alleviation, amelioration or treatment of pruritus, wherein the exosomes are economically isolated and purified in a large amount from the conditioned media of stem cells obtained after culturing stem cells that can be mass-cultured. For example, adipose-derived stem cells can be obtained in a large amount by a simple procedure such as liposuction. Adipose has about 40 times higher stem cells than bone marrow, umbilical cords or umbilical cord blood has. Thus, these adipose-derived stem cells have the lowest commercial cost and are obtained in a large amount. However, since adipose contains a large amount of impurities such as cell debris, waste, proteins and macroparticles, it is difficult to economically isolate a large amount of exosomes, which have high purity and a uniform particle size distribution, from the conditioned media of adipose-derived stem cells. Thus, it appears that there are technical barriers to isolating a large amount of exosomes, which have high purity and a uniform particle size distribution, from the conditioned media of stem cells in terms of economy.

When the composition of the present invention is applied as a pharmaceutical composition, a skin external preparation or a cosmetic composition, the stem cell-derived exosomes contained in the composition as an active ingredient exhibit significant effects on the prevention, suppression, alleviation, amelioration or treatment of pruritus, and can overcome the safety problem of stem cells themselves or the conditioned media of stem cells. Thus, the stem cell-derived exosomes contained in the composition for preventing, suppressing, alleviating, ameliorating or treating pruritus according to the present invention prevent, suppress, alleviate, ameliorate or treat pruritus by a mechanism which is completely different from the mechanism of limited wrinkle amelioration and skin regeneration known in the conventional art, and it is to be understood that this effect is not at all predictable from the conventional art.

A composition for preventing, suppressing, alleviating, ameliorating or treating pruritus according to one embodiment of the present invention includes stem cell-derived exosomes as an active ingredient.

In the composition according to one embodiment of the present invention, the exosomes may be obtained by performing the following steps: (a) adding trehalose to a conditioned medium of stem cells; (b) filtering the conditioned medium having the trehalose added thereto; (c) isolating exosomes from the filtered conditioned medium by tangential flow filtration (TFF); and (d) adding trehalose to a buffer for diafiltration, and performing diafiltration on the isolated exosomes by TFF using the buffer having the trehalose added thereto.

In the composition according to one embodiment of the present invention, when trehalose is added to the buffer for diafiltration in step (d), exosomes having a uniform particle size distribution and high purity can be effectively obtained (see FIGS. 6A to 6E).

Meanwhile, in the present invention, trehalose serves to efficiently discriminate exosomes from impurities such as cell debris, waste, proteins and macroparticles.

In the composition according to one embodiment of the present invention, the diafiltration may be performed continuously or discontinuously. The diafiltration may be performed using a buffer having at least 4 times, preferably at least 6 to 10 times, more preferably at least 12 times volume of the isolated exosomes.

In the composition according to one embodiment of the present invention, TFF may be performed using either a TFF filter having a molecular weight cutoff (MWCO) of 100,000 Da (Dalton), 300,000 Da, 500,000 Da or 750,000 Da, or a 0.05 µm filter.

In the composition according to one embodiment of the present invention, step (c) may further comprise concentrating the isolated exosomes to a volume of 1/100 to 1/25 by the TFF.

In the composition according to one embodiment of the present invention, the filtered conditioned medium may be sonicated before the TFF.

In the composition according to one embodiment of the present invention, the exosomes may decrease the expression levels of IL-4, IL-31 and TSLP in skin tissue or skin cells.

In the composition according to one embodiment of the present invention, the type of stem cells is not particularly limited, but the stem cells may preferably be mesenchymal stem cells, for example, stem cells derived from adipose, bone marrow, umbilical cords or umbilical cord blood, more preferably adipose-derived stem cells. The adipose-derived stem cells are not particularly limited as long as they do not pose a risk of infection with a pathogen and do not cause immune rejection, but they are preferably human adipose-derived stem cells.

The composition according to the present invention may be effectively used for the prevention, suppression, alleviation, amelioration or treatment of pruritus caused by various factors as listed above.

The composition according to one embodiment of the present invention may be prepared as a pharmaceutical composition. When the composition according to one embodiment of the present invention is prepared as a pharmaceutical composition, the composition according to one embodiment of the present invention may be any formulation for oral or parenteral administration.

The pharmaceutical composition according to one embodiment of the present invention may include pharmaceutically acceptable carriers, excipients or diluents according to a conventional method. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. For use, the pharmaceutical composition according to one embodiment of the present invention may be formulated as oral dosage forms, such as powders, pills, tablets, capsules, suspensions, emulsions, syrups, granules, elixirs, aerosols, or the like, skin external preparations, suppositories, or sterile injectable solutions.

Administration of the pharmaceutical composition according to one embodiment of the present invention means introducing a desired substance into a patient by any appropriate method, and the pharmaceutical composition may be administered by any general route, as long as the substance can reach a target tissue. For example, the pharmaceutical composition according to one embodiment of the present invention may be administered orally or parenterally. Routes for parenteral administration may include transdermal administration, intraperitoneal administration, intravenous administration, intra-arterial administration, intramuscular administration, subcutaneous administration, intradermal administration, topical administration, intrarectal administration, and the like. However, the scope of the present invention is not limited thereto, and various administration methods known in the art are not excluded. Furthermore, the pharmaceutical composition according to one embodiment may be administered by any device through which an active ingredient may be delivered into a target tissue or cell. In addition, the effective amount of the pharmaceutical composition according to one embodiment of the present invention means the amount required for administration in order to achieve the effect of treating a disease.

Formulations for parenteral administration of the pharmaceutical composition according to the present invention sterilized aqueous solutions, non-aqueous solutions, suspensions, emulsions, lyophilized formulations, or suppositories. Formulations for parenteral administration of the pharmaceutical composition according to one embodiment of the present invention may also be prepared as injectable formulations. Injectable formulations according to one embodiment of the present invention may be aqueous injectable formulations, non-aqueous injectable formulations, aqueous suspension injections, non-aqueous suspension injections, solid injectable formulations which are used after dissolution or suspension, etc., but are not limited thereto. An injectable formulation according to one embodiment of the present invention may further comprise at least one of distilled water for injection, vegetable oils (e.g., peanut oil, sesame oil, camellia oil, etc.), monoglyceride, diglyceride, propylene glycol, camphor, estradiol benzoate, bismuth subsalicylate, arsenobenzol sodium, streptomycin sulfate, depending on the type thereof, and may optionally further comprise a stabilizer or a preservative.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the kind of patient's disease, the severity of disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Meanwhile, when the composition according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation according to one embodiment of the present invention may include, in addition to stem cell-derived exosomes, a pruritus-treating agent and/or a moisturizer, which is used in the art, within the range that does not impair the effect of stem cell-derived exosomes, that is, the effect of preventing, suppressing, alleviating, ameliorating or treating pruritus. For example, the exosomes of the present invention may be contained in or mixed with at least one of hydrogel, hyaluronic acid, salt of hyaluronic acid (e.g., sodium hyaluronate, etc.), or hyaluronate gel. In the skin external preparation according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or cosmetic composition may be applied to or soaked in at least one surface of a patch, a mask pack or a mask sheet.

When the skin external preparation according to one embodiment of the present invention is prepared as a cosmetic composition, it is used for the purpose of preventing, suppressing, alleviating or ameliorating pruritus, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or cosmetic composition according to one embodiment of the present invention contains components which are commonly used in skin external preparations and/or cosmetic products. For example, the skin external preparation and/or cosmetic composition may contain conventional adjuvants and carriers, such as antioxidants, stabilizers, solubilizers, vitamins, pigments, and fragrances. In addition, other components in each formulation for the skin external preparation and/or cosmetic composition may be suitably selected without difficulty by those skilled in the art depending on the type or intended use of skin external preparation and/or cosmetic composition.

Another embodiment of the present invention provides a cosmetic method for regulating mammalian skin conditions, except for treatment purposes, by using the cosmetic composition. In the cosmetic method of the present invention, regulating skin conditions means improving skin conditions and/or prophylactically regulating skin conditions, and improving skin conditions means a visually and/or tactilely perceivable positive change in the appearance and feeling of skin tissue.

The cosmetic method according to one embodiment of the present invention includes: (a) applying the cosmetic composition directly to a mammalian skin; or (b) contacting or attaching a patch, a mask pack or a mask sheet, which has the cosmetic composition applied thereto or soaked therein, to the mammalian skin; or sequentially performing (a) and (b).

The cosmetic method according to one embodiment of the present invention may further comprise performing iontophoresis by allowing a microcurrent to flow through the mammalian skin having the cosmetic composition applied thereto. In addition, the cosmetic method according to one embodiment of the present invention may further comprise contacting or attaching an iontophoresis device to the mammalian skin.

In the cosmetic method according to one embodiment of the present invention, the iontophoresis device may include at least one battery selected from the group consisting of flexible batteries, lithium-ion secondary batteries, alkaline batteries, dry cells, mercury batteries, lithium batteries, nickel-cadmium batteries, and reverse electrodialysis batteries, or may include a patch, a mask pack or a mask sheet provided with the at least one battery.

Still another embodiment of the present invention provides a method for preventing, suppressing, alleviating, ameliorating or treating pruritus comprising administering to a mammal a therapeutically effective amount of the pharmaceutical composition.

In the method for preventing, suppressing, alleviating, ameliorating or treating pruritus according to the present invention, the mammal may be humans, dogs, cats, rodents, horses, cattle, monkeys, or pigs.

Advantageous Effects

As described above, the composition of the present invention can act against pruritus-inducing multiple cytokine targets, for example, IL-4, IL-31 and TSLP, and thus can be widely applied against pruritus caused by various factors and can effectively suppress and alleviate pruritus. In addition, when the composition of the present invention is applied directly to human skin, it can remarkably ameliorate pruritus-associated clinical scores, erythema and the like. Thus, the composition of the present invention is useful as a pharmaceutical composition, a skin external preparation and a cosmetic composition for preventing, suppressing, alleviating, ameliorating or treating pruritus.

In addition, according to the present invention, stem cell-derived exosomes having a uniform particle size distribution and high purity can be obtained in large amounts at low costs. Thus, the present invention can provide a composition which contains as an active ingredient, stem cell-derived exosomes having excellent functional activity, in large amounts at low costs. Furthermore, the present invention makes it possible to scale-up processes and is also suitable for good manufacturing practice (GMP).

It should be understood that the scope of the present is not limited to the aforementioned effects.

BRIEF DESCRIPTION OF DRAWINGS

The patent or application file contains at least one drawing executed in color. Copies of this patent or patent application publication with color drawing(s) will be provided by the Office upon request and payment of the necessary fee.

"FIG. 4A" shows the particle size distribution and the number of particles obtained by tunable resistive pulse sensing (TRPS) analysis. "FIG. 4B" shows the particle size distribution and the number of particles obtained by nanoparticle tracking analysis (NTA). "FIG. 4C" shows different magnifications of particle images obtained by transmitted electron microscopy (TEM) analysis. "FIG. 4D" shows the results of Western blot analysis of exosomes obtained according to one embodiment of the present invention. "FIG. 4E" shows the results of flow cytometry for CD63 and CD81 in the analysis of markers for exosomes obtained according to one embodiment of the present invention.

FIGS. 5A to 5C show the results of NTA analysis of particle size distributions, which indicate that exosomes having a uniform particle size distribution and high purity are obtained by the addition of trehalose. As the amount of trehalose added increases, a particle size distribution with a single peak can be obtained.

FIGS. 6A to 6C show the results of NTA analysis that indicate particle size distributions obtained depending on whether or not trehalose was added in a process of preparing exosomes according to one embodiment of the present invention. "FIG. 6A" shows the results obtained when trehalose was added throughout the preparation process; "FIG. 6B" shows the results obtained in the case that conditioned media are freeze-stored and thawed, and then trehalose was added to the thawed media; and "FIG. 6C" shows the results obtained when no trehalose was added.

EXAMPLES

Figure 1:
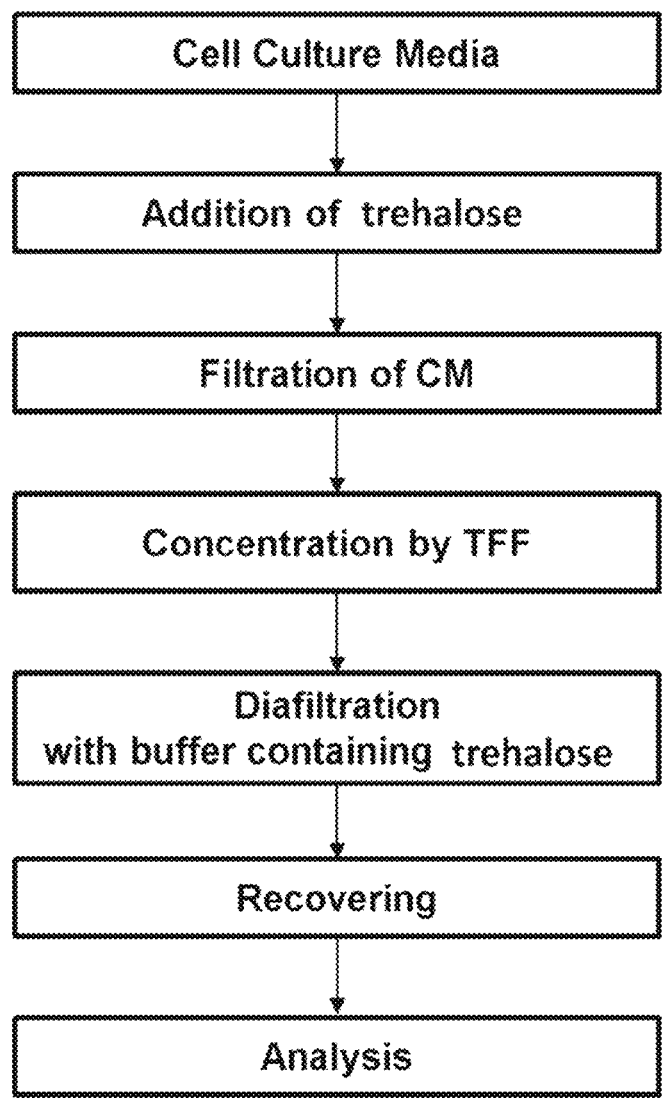
FIG. 1 is a flowchart illustrating a method of isolating and purifying exosomes in a method of preparing exosomes from culture media of stem cells according to one embodiment of the present invention.

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1

Cell Culture

Human dermal fibroblast HS68 cells purchased from ATCC were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$. Furthermore, human keratinocyte HaCaT cells were subcultured in DMEM medium supplemented with 10% FBS and 1 vol % penicillin-streptomycin at 37° C. under 5% $CO_2$.

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by TFF.

Example 2

Isolation and Purification of Exosomes by TFF Method

For isolating, concentrating and diafiltrating exosomes from the conditioned medium filtered through 0.22 μm filter in Example 1, TFF method was used. The filtered conditioned medium was sonicated to loose potential aggregation of exosomes before isolating and concentrating exosomes using TFF. As a filter for TFF method, a cartridge filter (known as a hollow fiber filter; purchased from GE Healthcare) or a cassette filter (purchased from Pall, Sartorius or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration. The diafiltration was performed continuously (continuous diafiltration) or discontinuously (discontinuous diafiltration), using a buffer having at least 4 times, preferably at least 6 to 10 times, more preferably at least 12 times volume of the isolated exosomes. To obtain exosomes having a uniform particle size distribution and high purity, 2 wt % trehalose in PBS was added to the buffer. FIGS. 6A to 6E show the results that by the addition of trehalose, exosomes having a uniform particle size distribution and high purity can be obtained in high yield.

Example 3

Analysis of Characteristics of Isolated Exosomes

Figure 2:
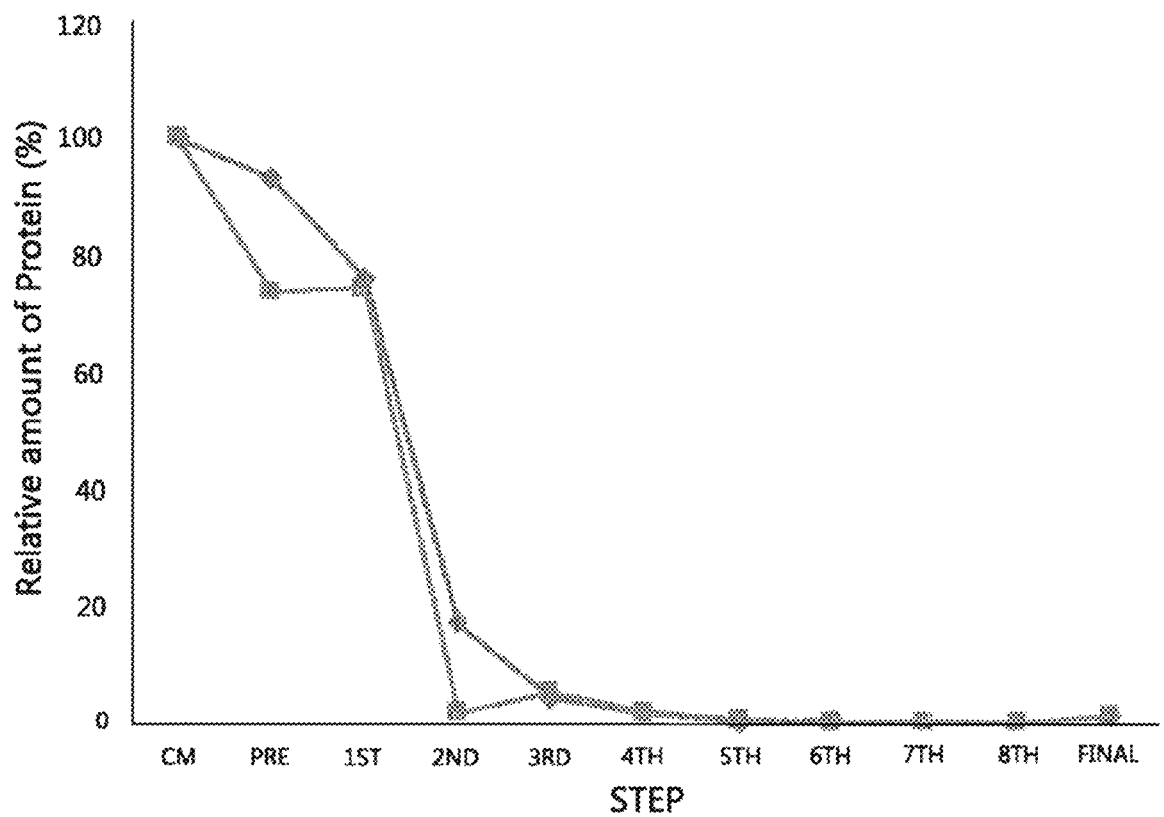
FIG. 2 shows the results of measuring the relative amount of proteins contained in a solution in each step of preparing exosomes from culture media of stem cells according to one embodiment of the present invention. The relative amount of proteins in each step was expressed as the relative ratio of the total amount of proteins in solution of each step to the total amount of proteins in conditioned media of stem cells. The experimental results as shown are the results obtained from two different batches, respectively.

The amounts of proteins of the isolated exosomes, the conditioned medium and the fractions of TFF isolation process were measured using BCA colorimetric assay (purchased from ThermoFisher Scientific) or FluoroProfile fluorescence assay (purchased from Sigma). With regard to exosomes isolated and concentrated by the TFF method according to one embodiment, the extent, to which proteins, lipids, nucleic acids, low-molecular-weight compounds, etc. were removed, was monitored by the protein assays, and the results of the monitoring are shown in FIG. 2. As a result, it could be seen that proteins present in the conditioned medium were very effectively removed by the TFF method according to one embodiment.

Figure 3:
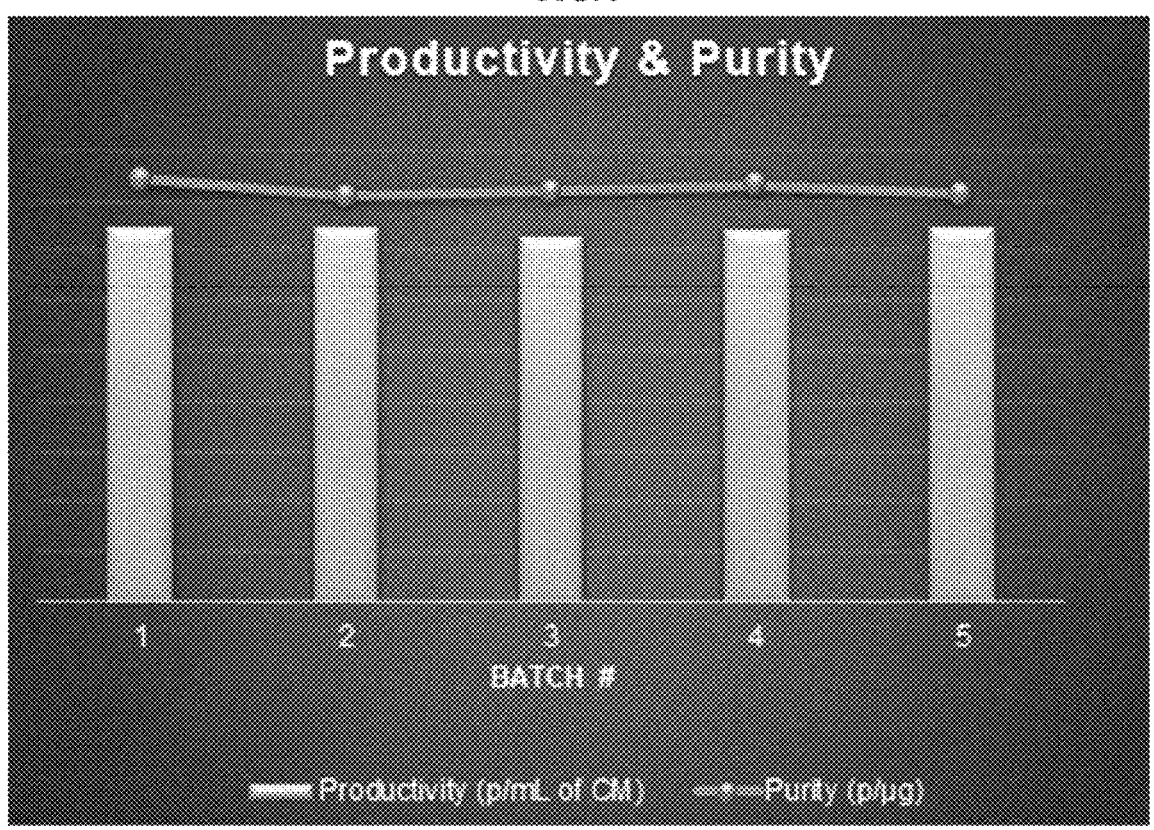
FIG. 3 shows the results of measuring the productivity and purity of exosomes obtained according to one embodiment of the present invention. The productivity of exosomes was calculated as the number of exosome particles obtained per mL of conditioned media of stem cells (CM), and the purity of exosomes was calculated as the number of exosome particles per μg of proteins contained in a final fraction. The experimental results as shown are the results obtained from five different batches, respectively.

FIG. 3 shows the results of comparing the productivity and purity of exosomes in each of five independent batches when exosomes were isolated by the TFF method according to one embodiment. The results obtained from the five independent batches were analyzed, and as a result, it was confirmed that exosomes were very stably isolated by the TFF method according to one embodiment.

Figure 4A:
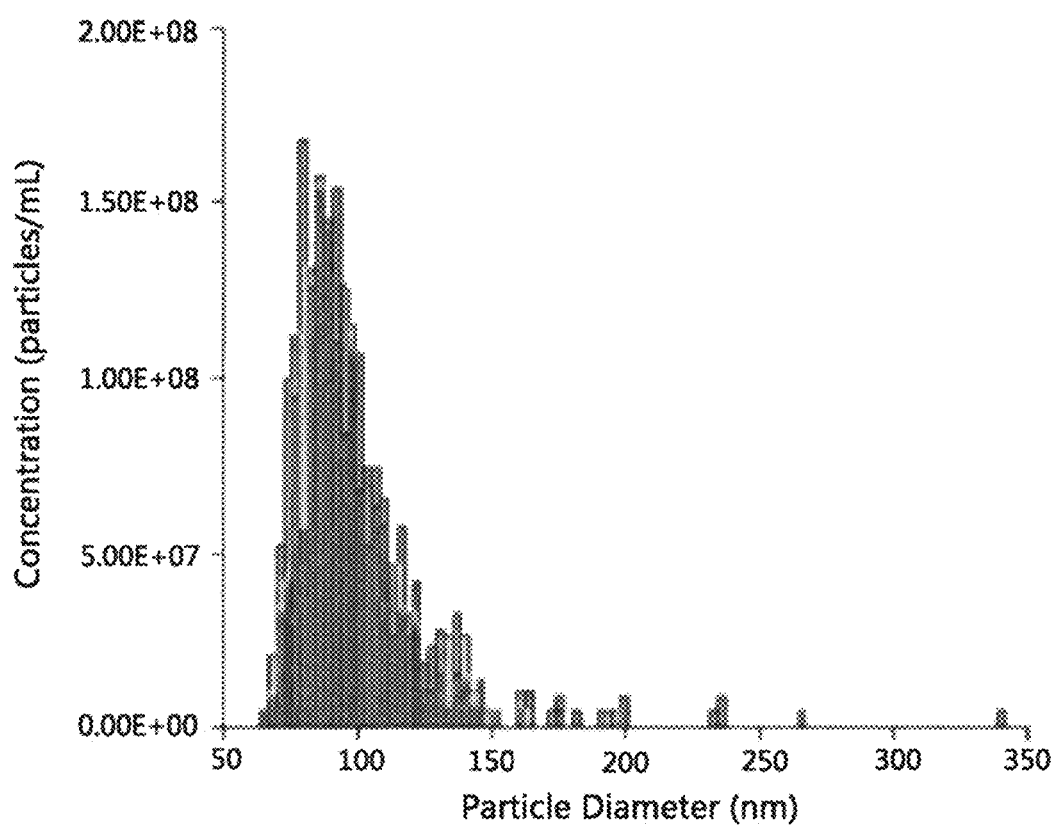
FIGS. 4A to 4E show the results of analyzing the physical properties of exosomes obtained according to one embodiment of the present invention.
Figure 4B:
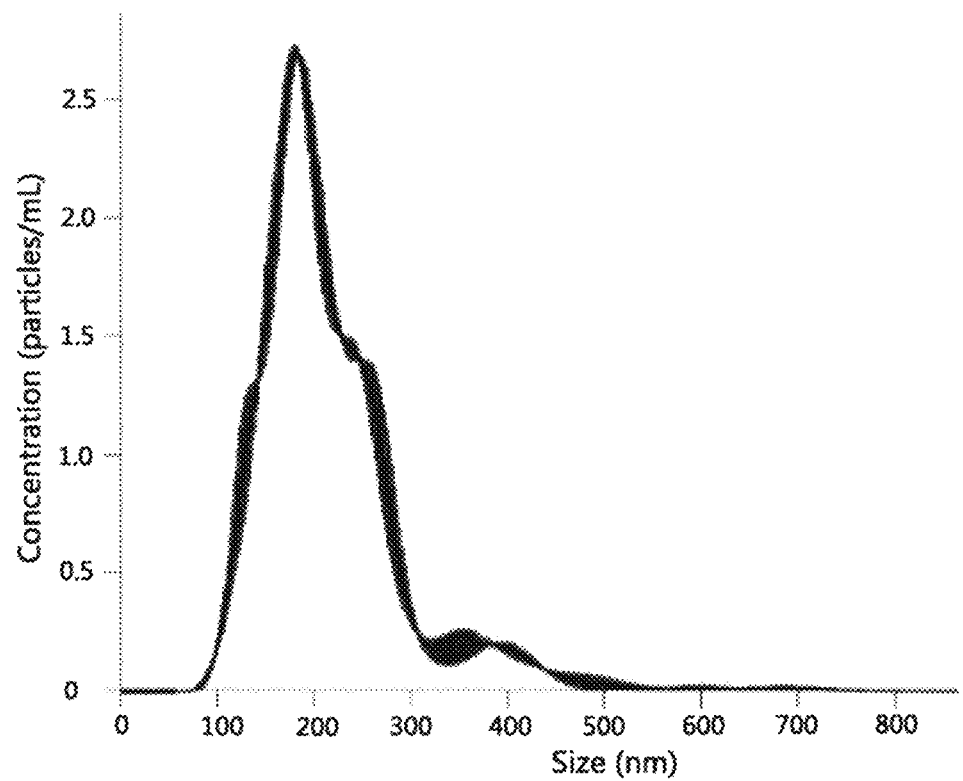
Figure 4C:
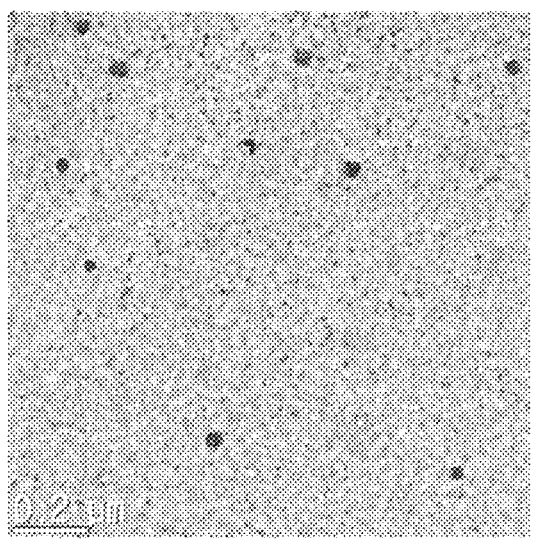
Figure 4C:
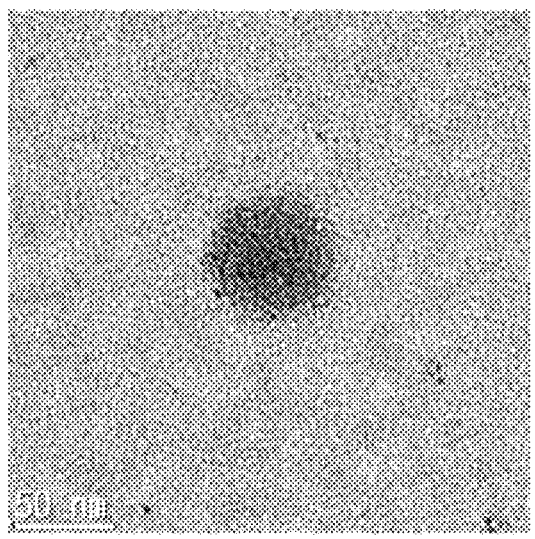

The particle size and concentration of the isolated exosomes were measured by nanoparticle tracking analysis (NTA) instrument (purchased from Malvern) or tunable resistive pulse sensing (TRPS) instrument (purchased from Izon Science). The uniformity and size of the isolated exosomes were analyzed by transmission electron microscopy (TEM). FIGS. 4A to 4C show the results of TRPS, NTA and TEM of the exosomes isolated by the isolation method according to one embodiment of the present invention.

Figure 5A:
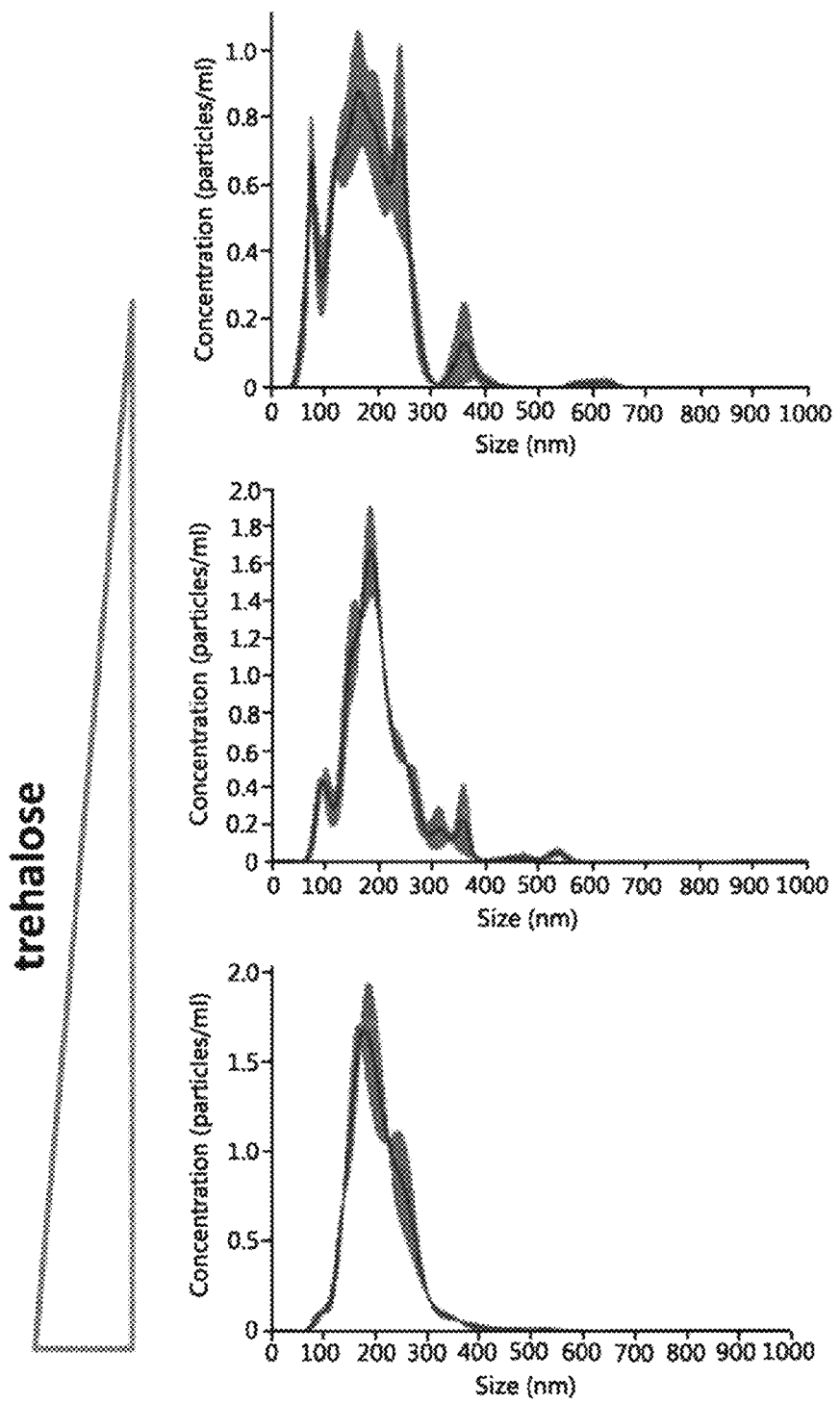
Figure 5C:
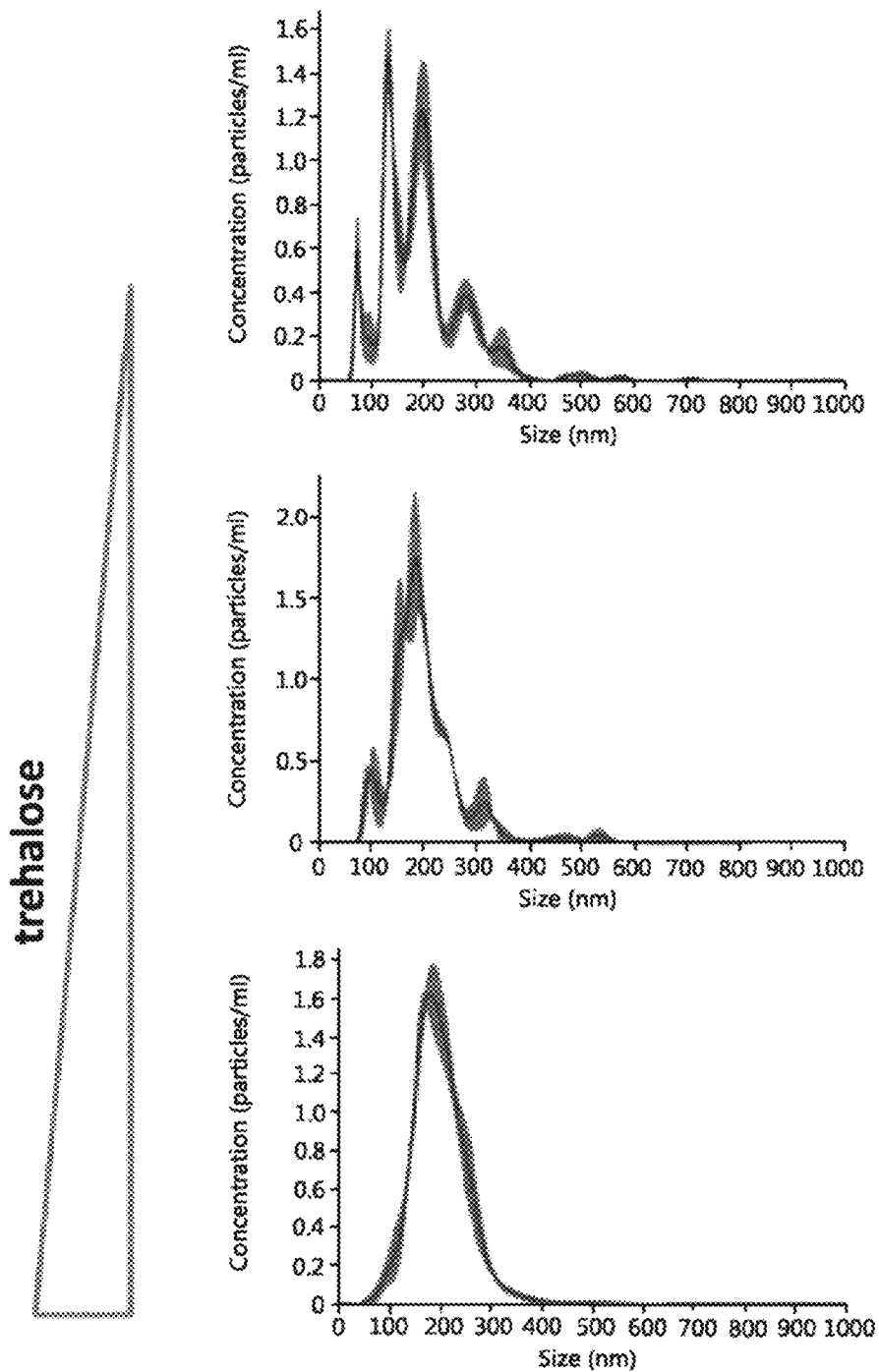

After exosomes were isolated, the size distribution of the exosomes was analyzed by NTA depending on whether trehalose was added. The results of the analysis are shown in FIGS. 5A to 5C. The concentration of trehalose was increased from 0 wt % to 1 wt % and 2 wt % (from the top to the bottom in FIGS. 5A to 5C), and the experiment was repeated three times. It was confirmed that when no trehalose was used, particles having a size of 300 nm or more were observed, whereas as the amount of trehalose added was increased, the number of particles having a size of 300 nm or more decreased and the size distribution of the exosomes became uniform.

Figure 6B:
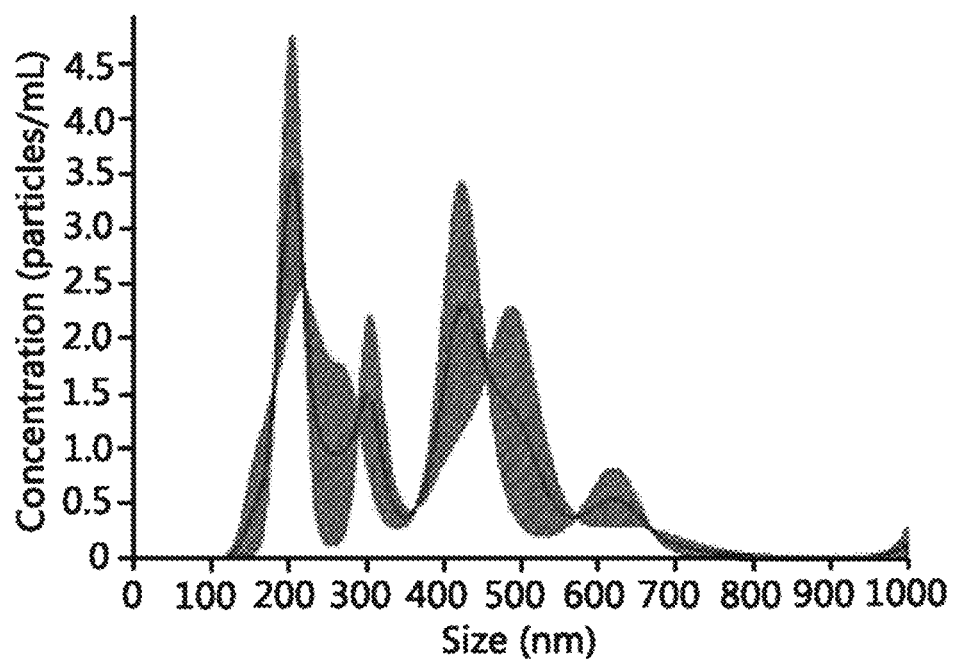
Figure 6C:
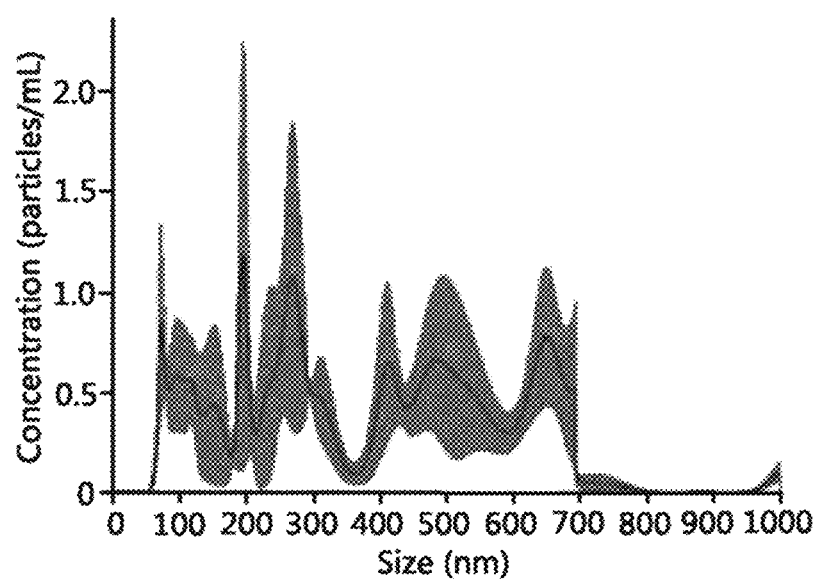

The effect due to the addition of trehalose in the process of isolating exosomes by the TFF method was additionally examined. As shown in FIGS. 6A to 6C, when 2 wt % trehalose in PBS was added throughout the process of preparing exosomes, exosomes having a uniform size distribution could be obtained (FIG. 6A). However, when the conditioned medium, which had been freeze-stored without adding trehalose, was used, but the TFF process was performed with adding trehalose only in the diafiltration process, or the TFF process was performed without adding any trehalose, uneven exosomes including a large amount of large particles were obtained (FIGS. 6B and 6C).

Figure 6D:
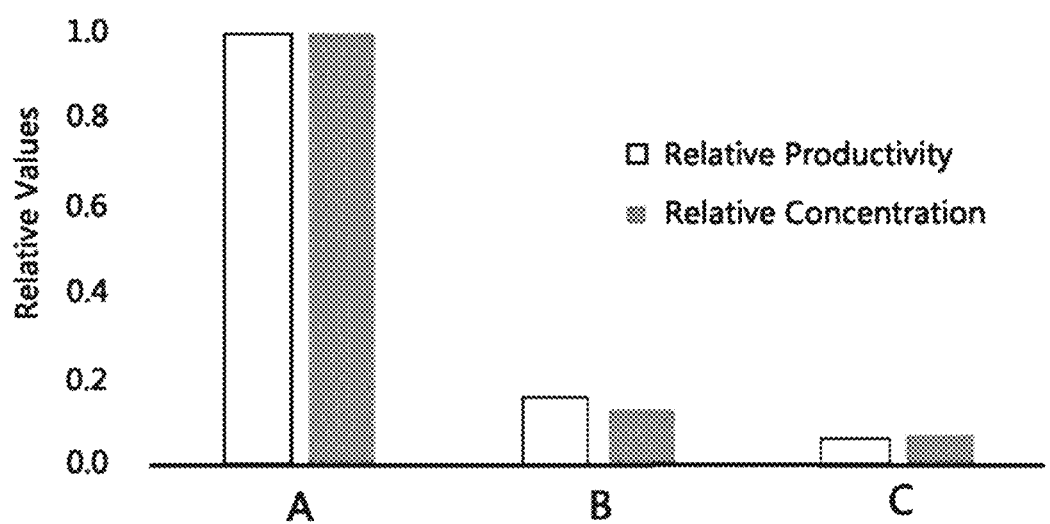
"FIG. 6D" shows the results of comparing the relative productivity and relative concentration of exosomes isolated by the methods of FIGS. 6A to 6C.
Figure 6E:
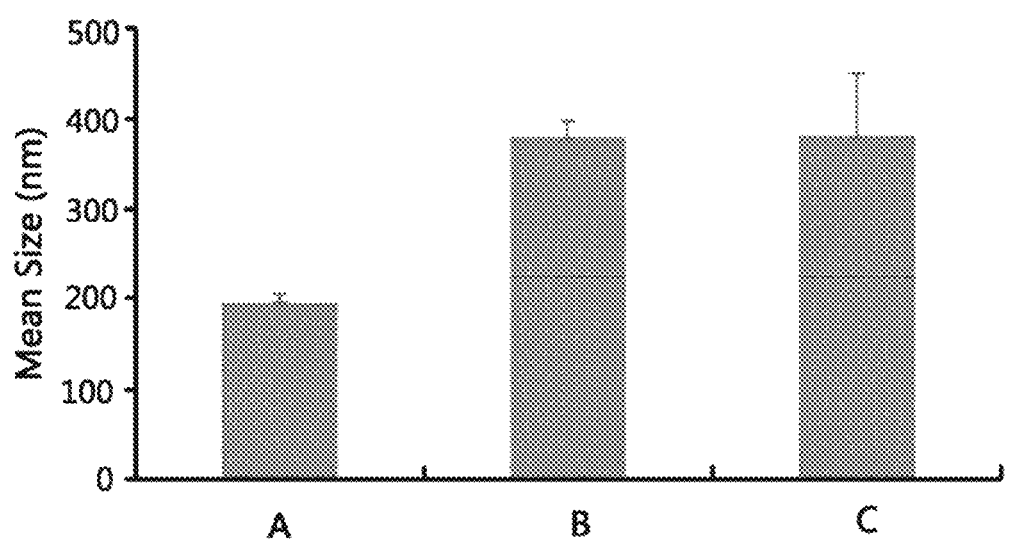
"FIG. 6E" shows the mean size of exosomes isolated by the methods of FIGS. 6A to 6C.

The relative productivity and concentration of the isolated exosomes were compared, and as a result, exosomes could be obtained with very high productivity when trehalose was added throughout the exosome production process. The obtained exosomes were at least 5 times concentration of the control (in which trehalose was not added throughout the exosome production process) (FIG. 6D). As shown in the NTA analysis result, it was confirmed that the mean size of the isolated exosomes was uniform (200 nm) when trehalose was added throughout the exosome production process (FIG. 6E).

Figure 4D:
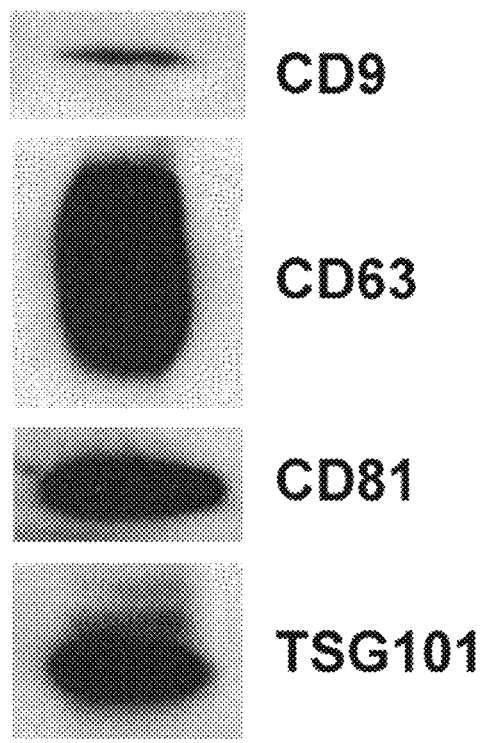

FIG. 4D shows the results of Western blot analysis of the exosomes isolated by the isolation method according to one embodiment of the present invention. As shown therein, the presence of CD9, CD63, CD81 and TSG101 markers was confirmed. As antibodies for each of the markers, anti-CD9 (purchased from Abcam), anti-CD63 (purchased from System Biosciences), anti-CD81 (purchased from System Biosciences) and anti-TSG101 (purchased from Abcam) were used, respectively.

Figure 4E:
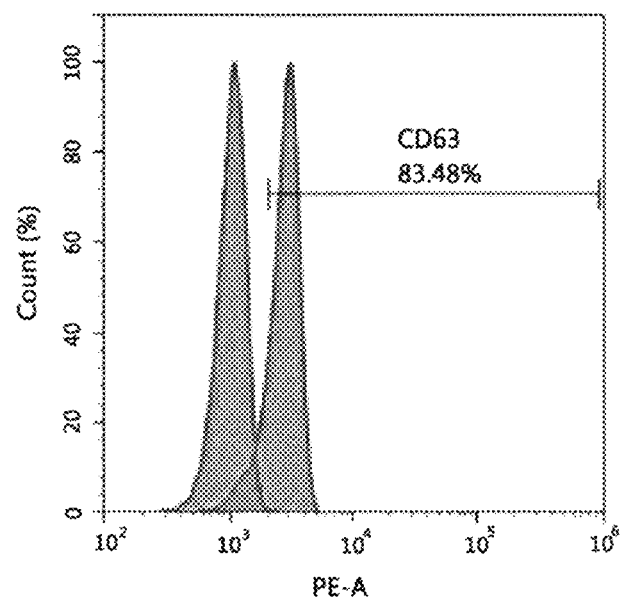
Figure 4E:
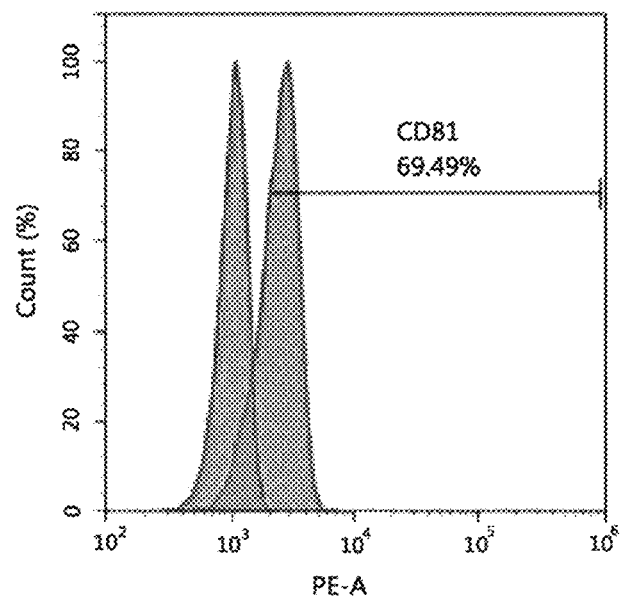

FIG. 4E shows the results of flow cytometry of the exosomes isolated by the isolation method according to one embodiment of the present invention. As shown therein, the presence of CD63 and CD81 markers was confirmed. To isolate CD63-positive exosomes, an Exosome-Human CD63 Isolation/Detection Reagent kit (purchased from ThermoFisher Scientific) was used according to the manufacturer's instruction. The markers were stained with PE-Mouse anti-human CD63 (purchased from BD) or PE-Mouse anti-human CD81 (purchased from BD), and then analyzed using a flow cytometer (ACEA Biosciences).

Taking the above results together, it could be confirmed that the isolation method according to one embodiment of the present invention could economically and efficiently isolate and purify exosomes having a uniform particle size distribution and high purity in high yield by adding trehalose in the isolation and/or purification process based on tangential flow filtration. In addition, it could be seen that the processes of the isolation method according to one embodiment of the present invention can be scaled-up and are also suitable for GMP.

Example 4

Measurement of Cytotoxicity Following Exosome Treatment

In order to evaluate the cytotoxicity of exosomes, isolated by the isolation method according to one embodiment of the present invention, in human skin fibroblast HS68 cells, the cells were treated with various concentrations of the exosomes, and the proliferation rate of the cells was examined. Specifically, HS68 cells were suspended in 10% FBS-containing DMEM, and then seeded and grown to 80 to 90% confluency and cultured in an incubator at 37° C. under 5% $CO_2$ for 24 hours. After 24 hours, the medium was removed, and the cells were treated with various concentrations of the exosomes prepared in Example 2. Then, the viability of the cells was evaluated while the cells were cultured for 24 to 72 hours. The cell viability was measured using WST-1 reagent (purchased from Takara), MTT reagent (purchased from Sigma), CellTiter-Glo reagent (purchased from Promega) or alamarBlue reagent (purchased from ThermoFisher Scientific) with a microplate reader (purchased from Molecular Devices).

Figure 14:
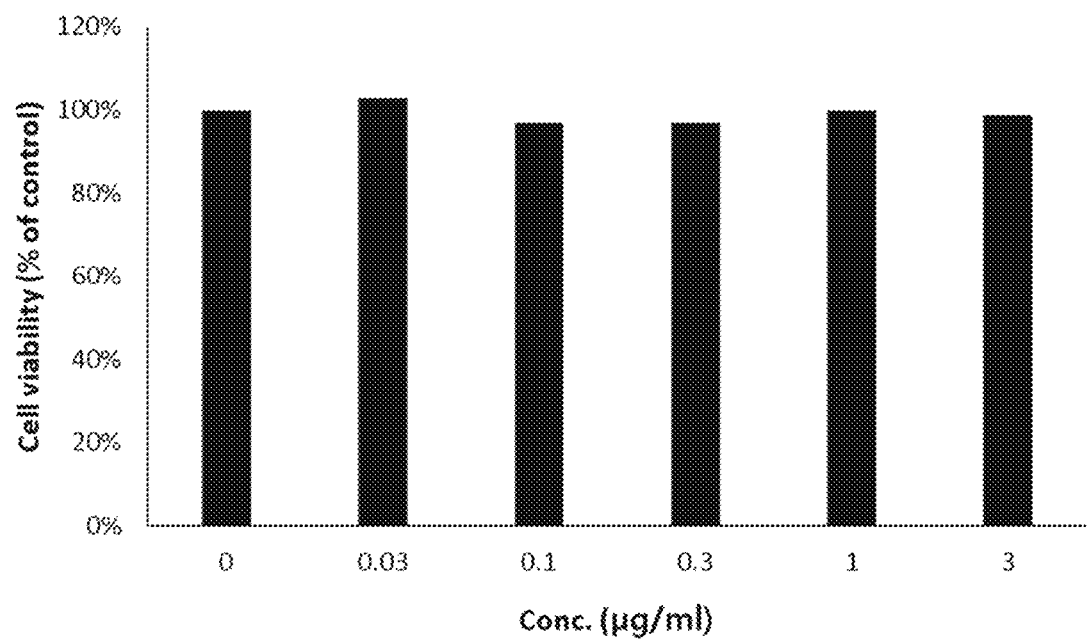
FIG. 14 shows results indicating that exosomes according to one embodiment of the present invention were not cytotoxic after human fibroblast HS68 cells were treated with the exosomes.

As a control, the cells cultured in conventional cell culture medium not treated with the exosomes was used. It was confirmed that the exosomes of the present invention showed no cytotoxicity in the concentration range used in the test (FIG. 14).

Example 5

Animal Model 1

Male NC/Nga mice (16 to 18 g, 5-week-old; purchased from Central Laboratory Animal Inc.) were purchased, adapted for 7 days, and then used in this experiment. The adapted mice were divided into five groups as follows after dermatitis with pruritus was induced in the mice.

(1) Normal: Normal control group;

(2) Vehicle (dermatitis-induced group): negative control group in which dermatitis with pruritus was induced by house dust mite extracts;

(3) IV: a test group in which the exosomes prepared in Example 2 were intravenously (IV) injected at a dose of 2.8 μg/head three times a week for two weeks, after dermatitis with pruritus was induced by house dust mite extracts;

(4) SC: a test group in which the exosomes prepared in Example 2 were subcutaneously (SC) injected at a dose of 2.8 μg/head three times a week for two weeks, after dermatitis with pruritus was induced by house dust mite extracts; and (5) Pred: a test group in which prednisolone was administered orally every day, after dermatitis with pruritus was induced by house dust mite extracts.

The auricles of each of NC/Nga mice (purchased from Central Laboratory Animal Inc.) was shaved with a razor, and then depilated by applying a suitable amount of a depilatory. After wiping off the depilatory, AD induction reagent (house dust mite extracts; purchased from BioStir Inc.) was applied uniformly to the auricles by a micropipette tip. After shaving with a razor, if necessary, 150 μL of 4% SDS aqueous solution was applied uniformly to the auricles by a micropipette tip. After the auricles were dried with cold air from a dryer and further dried naturally for about 2 to 3 hours, AD induction reagent was applied uniformly to the auricles by a micropipette tip. All the pretreatments were performed twice a week for 3 weeks, i.e. six times in total.

Before starting administration of the exosomes prepared in Example 2, clinical skin score assessment was performed. According to the ranked scores, the animals were randomly grouped so that the average score of each group was distributed as uniformly as possible.

Example 6

Animal Model 2

To evaluate the dose-dependent effect of exosomes, mice were divided into 9 groups as follows after dermatitis with pruritus was induced as described in Example 5 above.

Figure 8A:
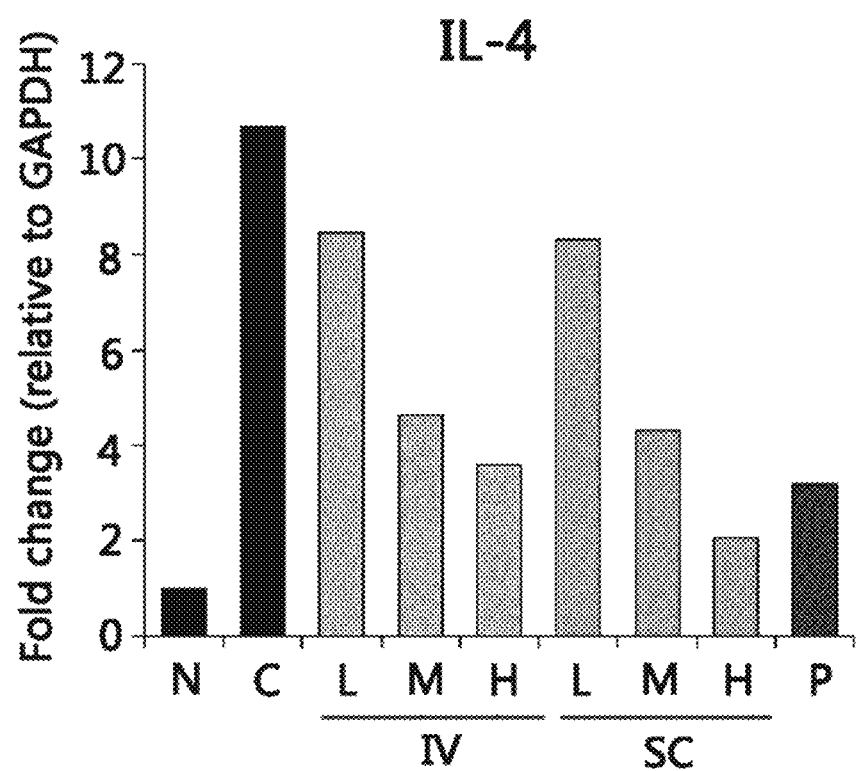
FIGS. 8A and 8B depict graphs showing the results of real-time PCR performed to examine changes in the mRNA expression levels of IL-4 and IL-31 (which cause pruritus) in samples obtained from skin lesion of animal model 2, after treating mice, in which atopy with pruritus was induced, with exosomes according to one embodiment of the present invention.
Figure 8B:
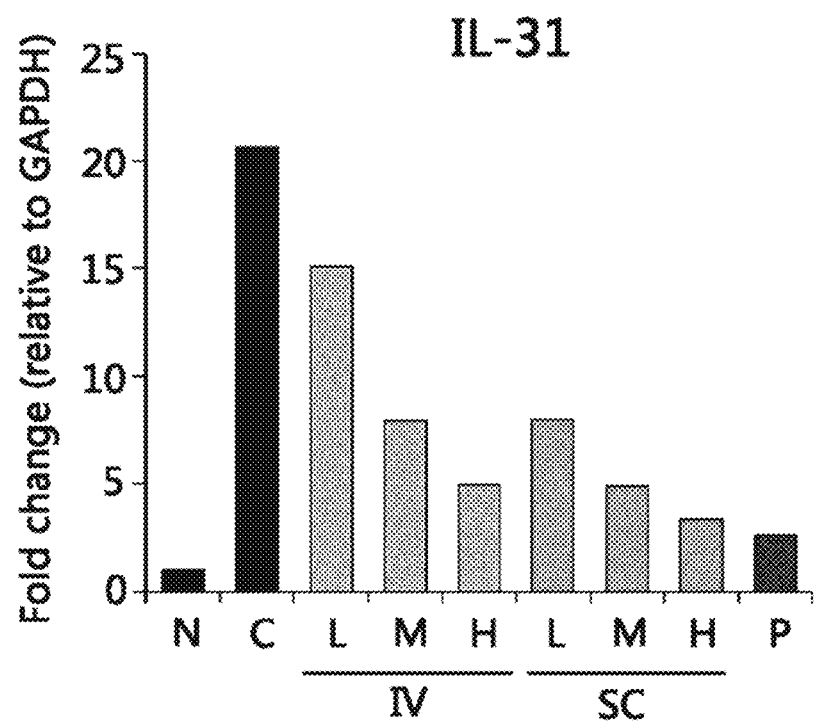

(1) Normal: normal control group (indicated by "N" in FIGS. 8A and 8B);

(2) Control (dermatitis-induced group): a negative control group in which dermatitis with pruritus was induced by house dust mite extracts (indicated by "C" in FIGS. 8A and 8B);

(3) IV, L (exosome, low): a test group in which the exosomes prepared in Example 2 above were intravenously (IV) injected at a dose of 0.14 μg/head three times a week for 4 weeks, after dermatitis with pruritus was induced by house dust mite extracts;

(4) W, M (exosome, medium): a test group in which the exosomes prepared in

Example 2 above were intravenously (IV) injected at a dose of 1.4 μg/head three times a week for 4 weeks, after dermatitis with pruritus was induced by house dust mite extracts;

(5) IV, H (exosome, high): a test group in which the exosomes prepared in Example 2 above were intravenously (IV) injected at a dose of 10 μg/head three times a week for 4 weeks, after dermatitis with pruritus was induced by house dust mite extracts;

(6) SC, L (exosome, low): a test group in which the exosomes prepared in Example 2 above were subcutaneously (SC) injected at a dose of 0.14 µg/head three times a week for 4 weeks, after dermatitis with pruritus was induced by house dust mite extracts;

(7) SC, M (exosome, medium): a test group in which the exosomes prepared in Example 2 above were subcutaneously (SC) injected at a dose of 1.4 µg/head three times a week for 4 weeks, after dermatitis with pruritus was induced by house dust mite extracts;

(8) SC, H (exosome, high): a test group in which the exosomes prepared in Example 2 above were subcutaneously (SC) injected at a dose of 10 µg/head three times a week for 4 weeks, after dermatitis with pruritus was induced by house dust mite extracts; and (9) Pred: a test group in which prednisolone was administered orally every day, after dermatitis with pruritus was induced by house dust mite extracts (indicated by "P" in FIGS. 8A and 8B).

Dermatitis induction was performed as described in Example 5, and an excessive amount of AD induction reagent was applied so that the mean clinical skin score at the time of administration of the exosomes was 9. Before starting administration of the exosomes prepared in Example 2, clinical skin score assessment was performed. According to the ranked scores, the animals were randomly grouped so that the average score of each group was distributed as uniformly as possible.

Example 7

Measurement of mRNA Expression Levels of Cytokines

In order to examine whether the exosomes of the present invention have the effect of suppressing and alleviating pruritus and whether the exosomes can be widely applied against pruritus caused by various factors, the mRNA expression levels of IL-4 and IL-31 were analyzed. IL-4 is widely known as a pruritus-inducing cytokine, and it was reported that skin pruritus is induced in transgenic mice expressing IL-4 in the epidermis (Journal of Investigative Dermatology (2001) 117, pp. 977-983). In addition, it was reported that IL-31 is overexpressed in atopic dermatitis patients showing pruritus and that pruritus is induced in transgenic mice overexpressing IL-31 (J Allergy Clin Immunol (2006) 117, pp. 411-417). Furthermore, it was reported that IL-31 induces pruritus by binding to 31RA/OSMR receptor (European Journal of Allergy and Clinical Immunology (2018) 73, pp. 29-36) and that treatment with an antibody against IL-31 receptor A alleviates pruritus (New England Journal of Medicine (2017) 376; 9, pp. 826-835). Accordingly, if the production or expression levels of IL-4 and IL-31 in skin tissue or blood are analyzed after treatment with a candidate substance, the effects of the candidate substance on the suppression and alleviation of pruritus could be evaluated.

First, animals from animal model 1 of Example 5 and animal model 2 of Example 6 were sacrificed and the tissue of skin lesion site was dissected therefrom. Thereafter, from the total RNA obtained from the tissue dissected from animals from animal model 1, cDNA was synthesized and subjected to real-time PCR. The changes in the mRNA expression levels of IL-4 and IL-31 which are the major causes of pruritus were measured by the real-time PCR. In addition, from the total RNA obtained from the tissue dissected from animals of animal model 2, cDNA was synthesized and subjected to real-time PCR. The changes in the mRNA expression levels of IL-4 and IL-31 which are the major causes of pruritus were measured by the real-time PCR. As a reference gene for normalizing the above genes expression, GAPDH gene was used. The sequences of primers used in the real-time PCR are shown in Table 1 below.

TABLE 1

Nucleotide Sequences of Primers used in Real-Time PCR

| | Sequences | |
|---|---|---|
| Genes | Forward primer (5' → 3') | Reverse primer (5' → 3') |
| IL-4 | ACA GGA GAA GGG ACG CCA T (SEQ ID NO: 1) | GAA GCC CTA CAG ACG AGC T CA (SEQ ID NO: 2) |
| IL-31 | CAC ACA GGA ACA ACG AAG C C (SEQ ID NO: 3) | CGA TAT TGG GGC ACC GAA G (SEQ ID NO: 4) |
| GAPDH | CAT GGC CTT CCG TGT TCC TA (SEQ ID NO: 5) | CCT GCT TCA CCA CCT TCT TG A T (SEQ ID NO: 6) |

Figure 7A:
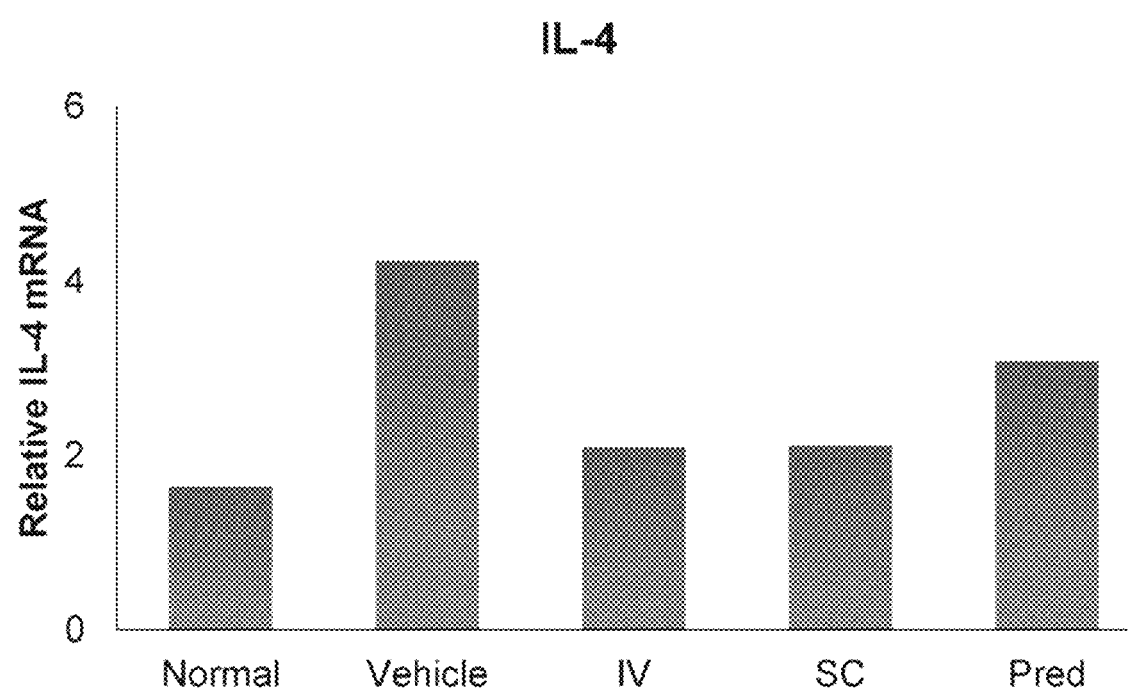
FIGS. 7A and 7B depict graphs showing the results of real-time PCR performed to examine changes in the mRNA expression levels of IL-4 and IL-31 (which cause pruritus) in samples obtained from skin lesion of animal model 1, after treating mice, in which atopy with pruritus was induced, with exosomes according to one embodiment of the present invention.
Figure 7B:
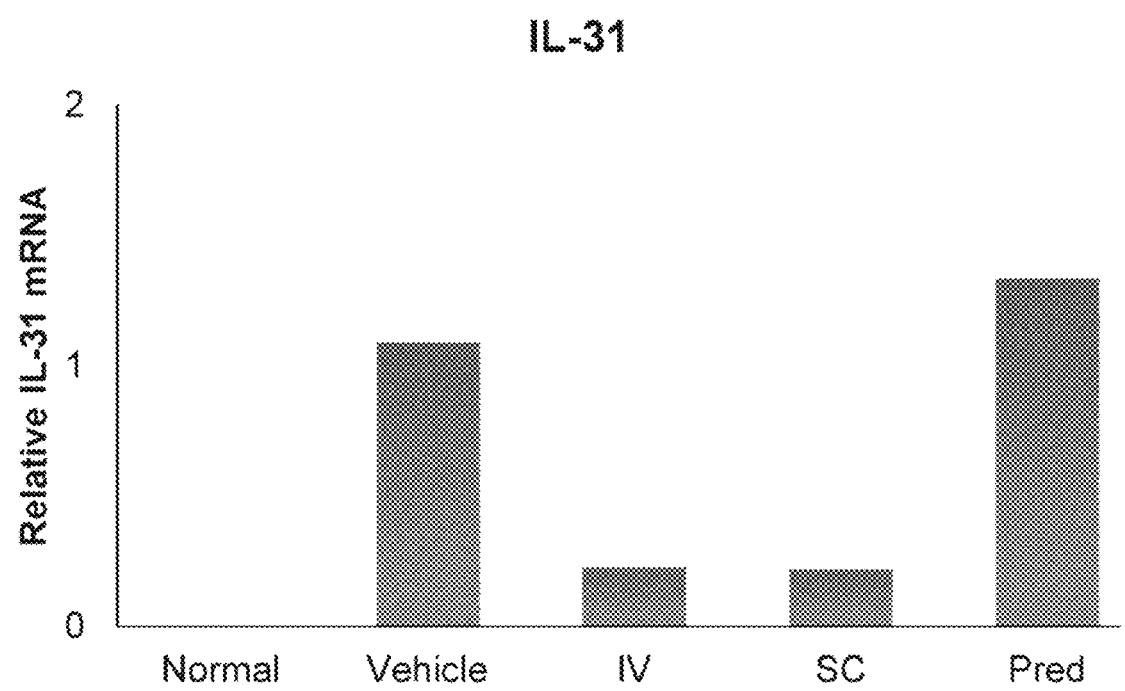

Through the experiment on animal model 1, it was confirmed that the expression levels of both IL-4 and IL-31 (which cause pruritus) in all the groups (IV and SC) treated with the exosomes of the present invention decreased (FIGS. 7A and 7B). In addition, through the experiment on animal model 2, it was confirmed that the expression levels of both IL-4 and IL-31 (which cause pruritus) in all the groups (IV and SC) treated with the exosomes of the present invention decreased in a dose-dependent manner (FIGS. 8A and 8B). Thus, the exosomes of the present invention are able to act against both of IL-4 and IL-31 (which are major targets causing pruritus), and thus are able to be widely applied against pruritus caused by various factors and can effectively suppress and alleviate pruritus.

Example 8

Measurement of TSLP Suppressing Effect Using HaCaT Cells

It is known that TSLP is overexpressed in human epithelial cells or keratinocytes of patients with severe pruritus and is a substance that causes skin pruritus. Thus, by confirming if a specific candidate substance suppresses TSLP induced in skin keratinocytes or not, the effect of the candidate substance on the suppression or alleviation of pruritus can be confirmed. Human keratinocyte HaCaT cells were suspended in DMEM (purchased from ThermoFisher Scientific) supplemented with 10% FBS, 1% amphotericin B (purchased from Sigma) and 1% penicillin-streptomycin, and then seeded into each well of a 12-well plate at a density of $1\times10^5$ cells and cultured for 24 hours. Next, the cells were additionally cultured in serum-free DMEM medium for 24 hours. Then, the adherent cells were washed twice with PBS, and in serum-free medium, not treated or treated with Poly I:C (purchased from Sigma) and histamine (purchased from Sigma) without or with the exosomes of the present invention (exosomes prepared in Example 2) according to the groups shown in FIG. 9A, and cultured for 24 hours. From RNA isolated from HaCaT cells of each group, cDNA was synthesized and subjected to real-time PCR, and the change in the mRNA expression level of TSLP which is the major cause of pruritus was measured by the real-time PCR. As a reference gene for normalizing the TSLP gene expression, β-actin gene was used. The sequences of primers used in the real-time PCR are shown in Table 2 below.

TABLE 2

Nucleotide sequences of primers used in real-time PCR

| Genes | Forward primer (5' → 3') | Reverse primer (5' → 3') |
|---|---|---|
| TSLP | GCTATCTGGTGCCCAGGCTAT (SEQ ID NO: 7) | CGACGCCACAATCCTTGTAAT (SEQ ID NO: 8) |
| β-actin | GGCCATCTCTTGCTCGAAGT (SEQ ID NO: 9) | GACACCTTCAACACCCCAGC (SEQ ID NO: 10) |

In addition, human keratinocyte HaCaT cells were suspended in DMEM (purchased from ThermoFisher Scientific) supplemented with 10% FBS (fetal bovine serum), 1% amphotericin B (purchased from Sigma) and 1% penicillin-streptomycin, and then seeded into each well of a 6-well plate at a density of $5\times10^5$ cells and cultured for 24 hours. Next, the cells were additionally cultured in serum-free DMEM medium for 24 hours. Then, the adherent cells were washed twice with PBS, and in serum-free medium, not treated or treated with Poly I:C (purchased from Sigma) without or with the exosomes of the present invention (exosomes prepared in Example 2) according to the groups shown in FIG. 9B, and cultured for 24 hours. In each group, the amount of TSLP protein was measured by Western Blotting using TSLP antibody (Abcam, Cambridge, Mass.). The amount of protein was quantified by BCA assay using BSA (bovine serum albumin) as a reference material. The amount of TSLP protein in each group was normalized by the amount of GAPDH protein.

Figure 9A:
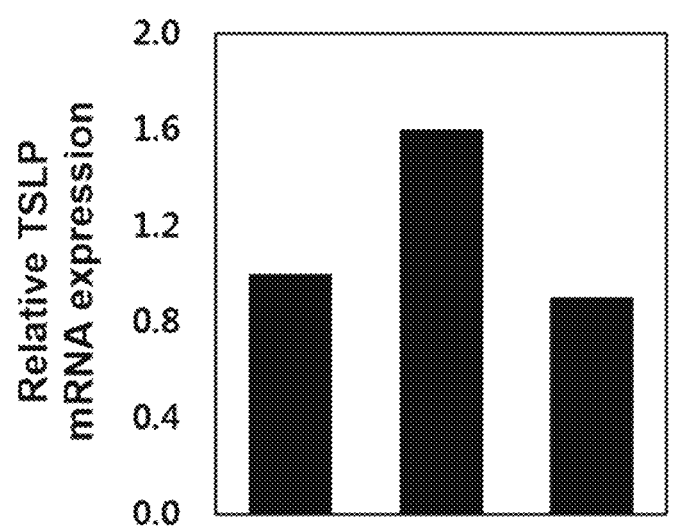
FIGS. 9A and 9B show results indicating that the mRNA expression and protein production of TSLP decreased when human keratinocyte HaCaT cells were treated with exosomes according to one embodiment of the present invention.
Figure 9B:
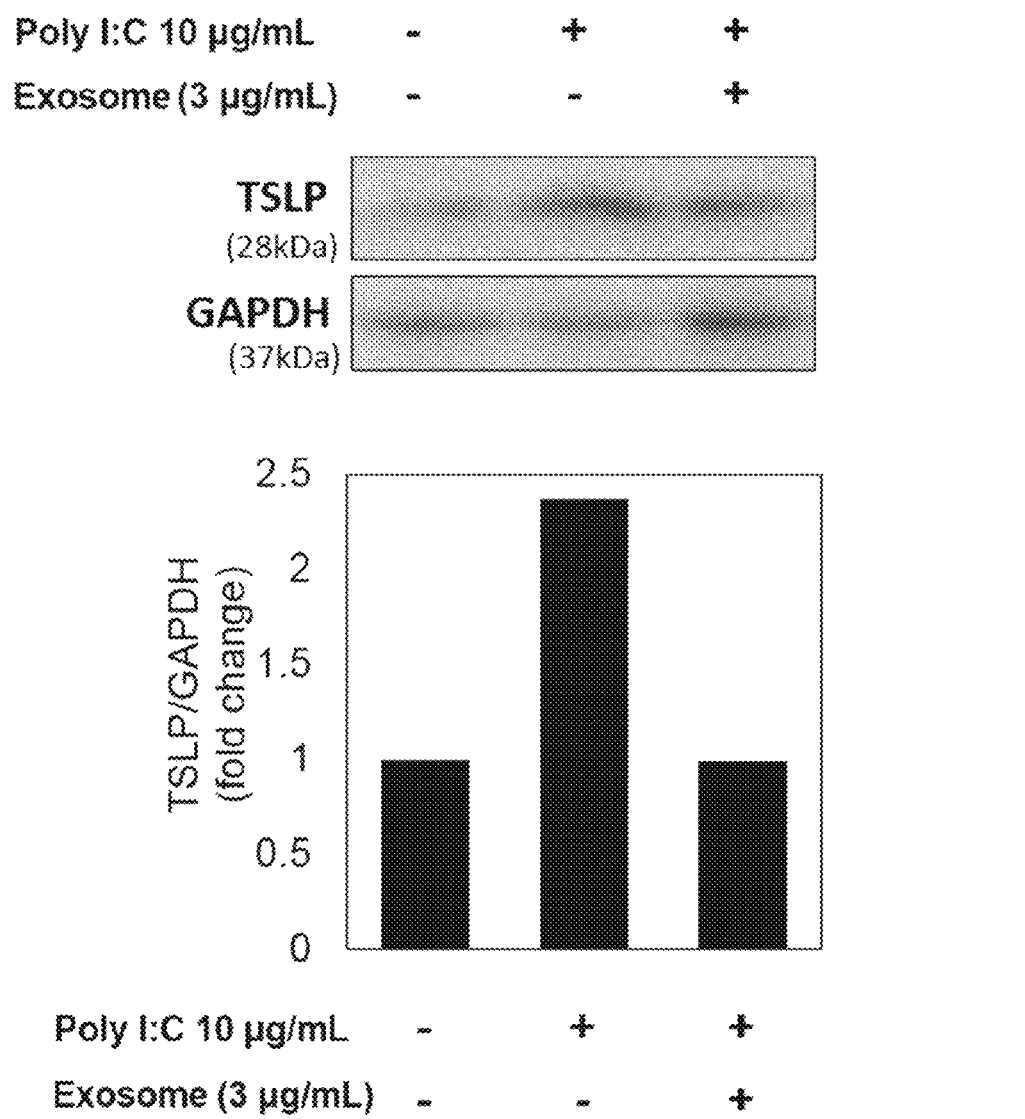

As a result, it was confirmed that the exosomes of the present invention decreased the mRNA expression level and protein production of TSLP (which causes pruritus) in skin keratinocytes (FIGS. 9A and 9B). Thus, the exosomes of the present invention are able to act against TSLP (which is a major target causing pruritus), and thus effectively suppress and alleviate pruritus.

Example 9

Test for Skin Penetration Ability of Exosomes

Figure 10:
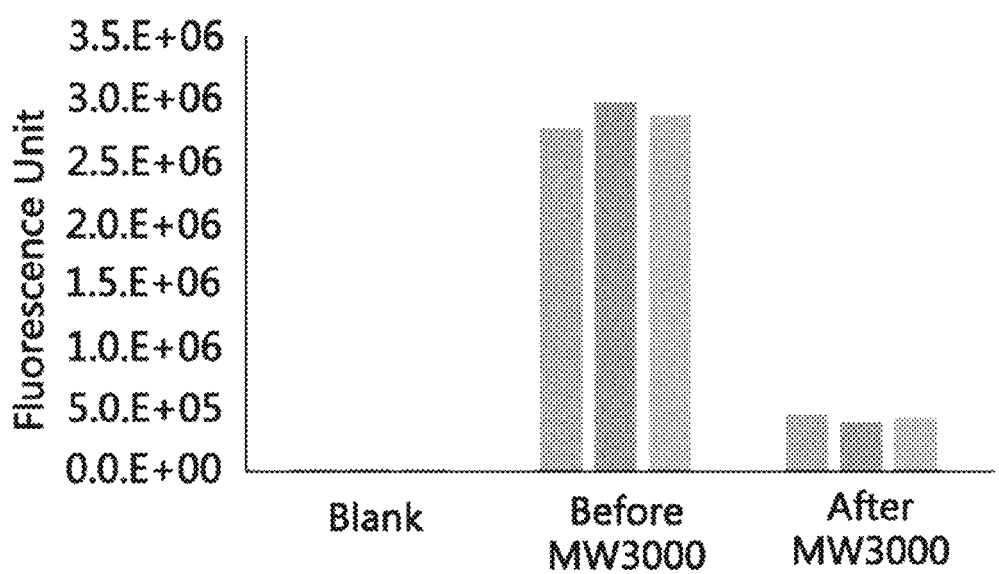
FIG. 10 shows the results of measuring fluorescence intensity to identify exosomes stained with PKH67.

To prepare fluorescently stained exosomes, PKH67 dye (purchased from Sigma) was used. 1 mM PKH67 was diluted in Diluent C (purchased from Sigma) to prepare 10 μM PKH67 solution. The solution was mixed with a suitable concentration of exosome solution and allowed to react at room temperature under a light-shielded condition for 10 minutes. After completion of the reaction, MW3000 spin column (purchased from ThermoFisher Scientific) was used to remove the remaining free PKH67 dye from the exosomes stained with PKH67 (hereinafter, abbreviated as "PKH-exosomes"). After removing PKH67 that did not react with the exosomes, analysis was performed using a fluorometer (purchased from Molecular Devices), and as a result, it was confirmed that fluorescence with sufficient intensity was detected in the PKH-exosomes (FIG. 10).

Figure 11:
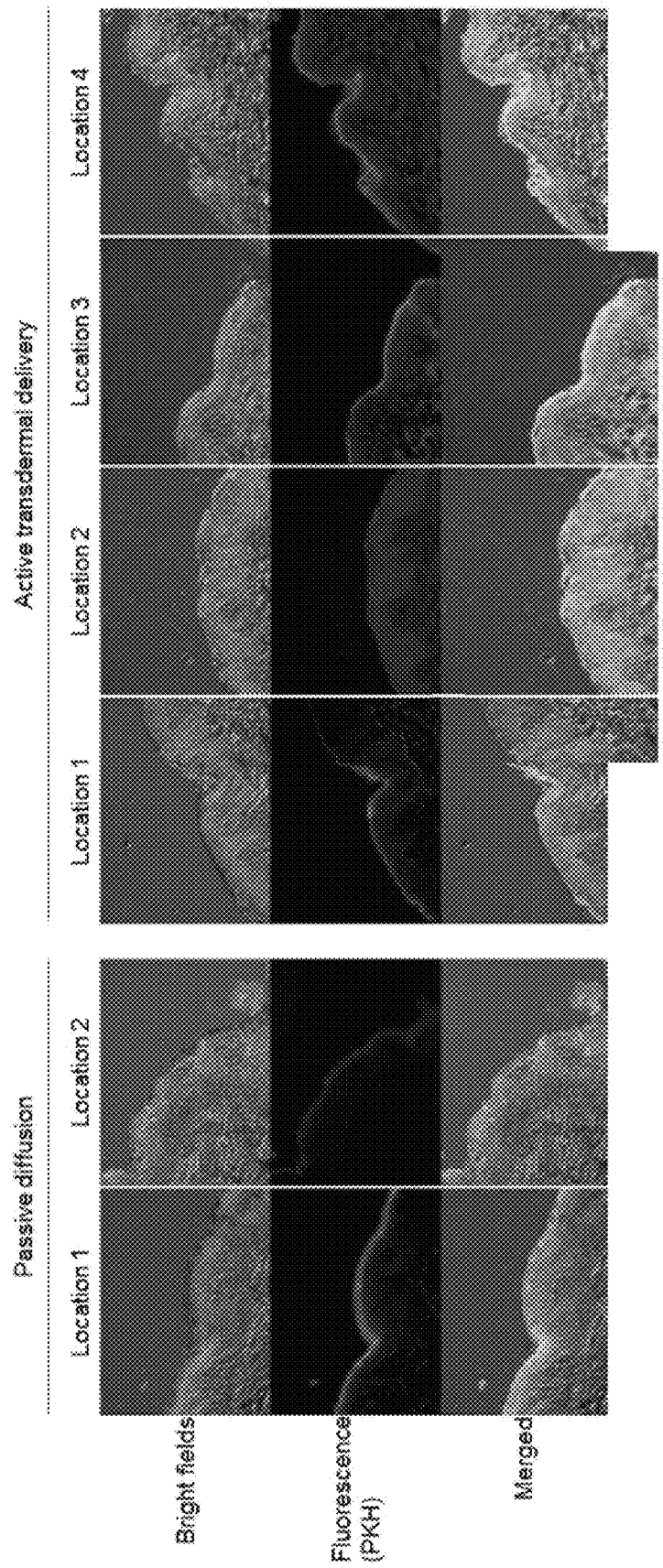
FIG. 11 depicts fluorescence microscopic images showing the extent to which fluorescently stained exosomes were delivered into porcine skin tissue.

The PKH-exosomes were dispersed in phosphate buffered saline (PBS) at a suitable concentration, for example, a concentration of $1\times10^5$ particles/mL to $1\times10^9$ particles/mL, and applied to the outer surface of porcine skin. The porcine skin was covered with nonwoven fabric to prevent drying of the PKH-exosome solution, and then the PKH-exosomes and the skin tissue allowed to react for a suitable time, for example 30 minutes to 1 hour, so that the PKH-exosomes reached the subcutaneous tissue of the porcine skin. Alternatively, after the PKH-exosomes were applied to the outer surface of the porcine skin and the skin was covered with nonwoven fabric, a microcurrent was allowed to flow through the skin for a predetermined time, for example, 30 minutes to 1 hour. After completion of the reaction, the porcine skin tissue was fixed overnight in 3.7% formaldehyde solution, and washed three times with PBS for 5 minutes each time. The washed porcine skin tissue was soaked in 30% sucrose solution, and then treated with OCT compound. Next, the tissue was washed three times with PBS for 5 minutes each time, and then sectioned using a microtome. The tissue section was placed on a slide glass. Meanwhile, preparation of the tissue section may be performed before the tissue is fixed with formaldehyde solution. The fluorescence detected from the PKH-exosomes in the tissue section was observed using a fluorescence microscope. As a result, it was confirmed that the PKH-exosomes were delivered through the epidermis of the porcine skin tissue into the subcutaneous tissue (FIG. 11). As shown in FIG. 11, the exosomes of the present invention could effectively penetrate through the skin barrier, so that it could be delivered deep into the skin tissue and effectively absorbed into the skin.

Therefore, a skin external preparation or cosmetic composition containing the exosomes as an active ingredient will effectively act in the prevention, suppression, alleviation, amelioration or treatment of pruritus.

Figure 12:
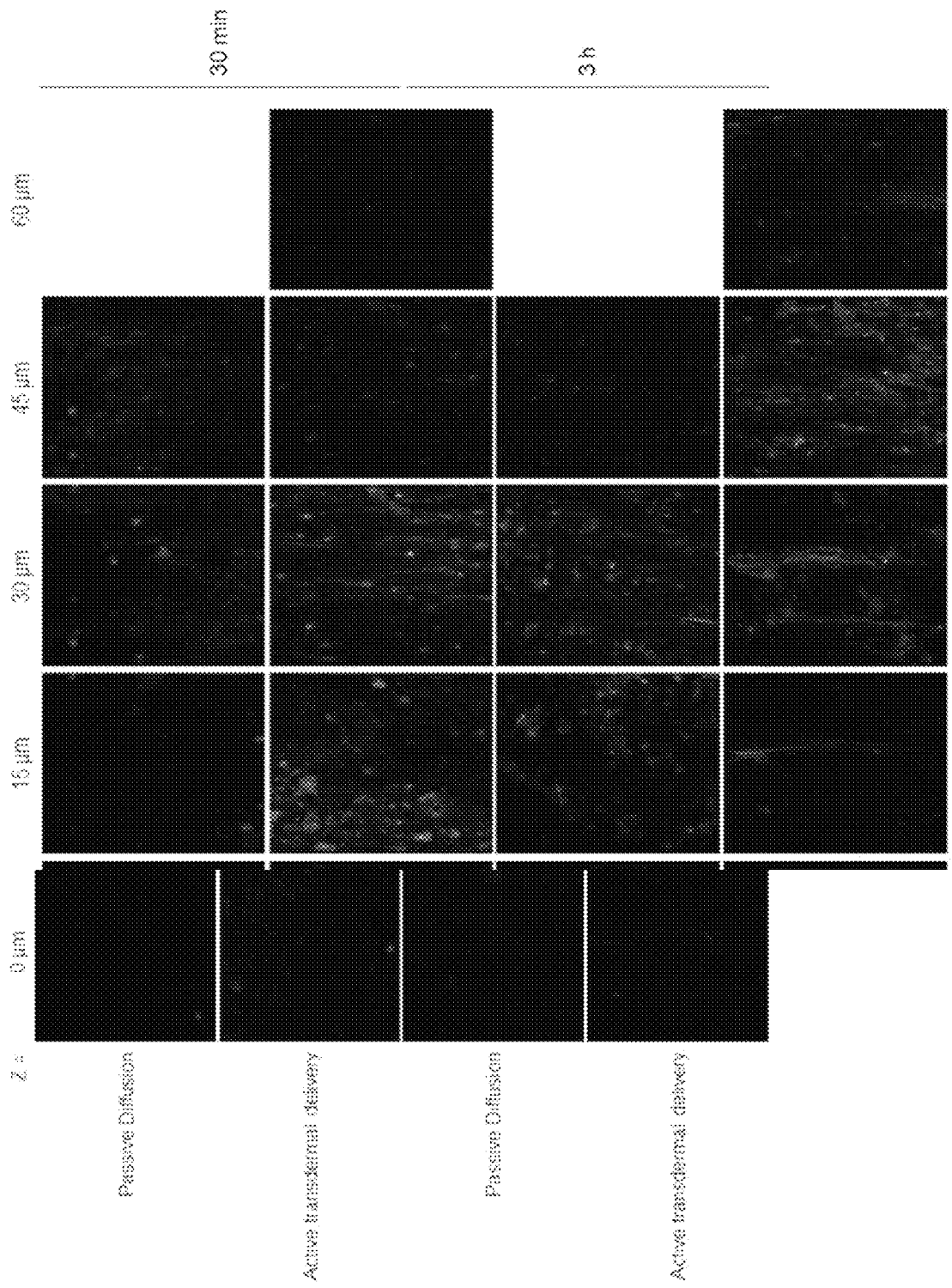
FIG. 12 depicts confocal fluorescence microscopic images showing the extent to which fluorescently stained exosomes were delivered into mouse skin tissue.
Figure 13:
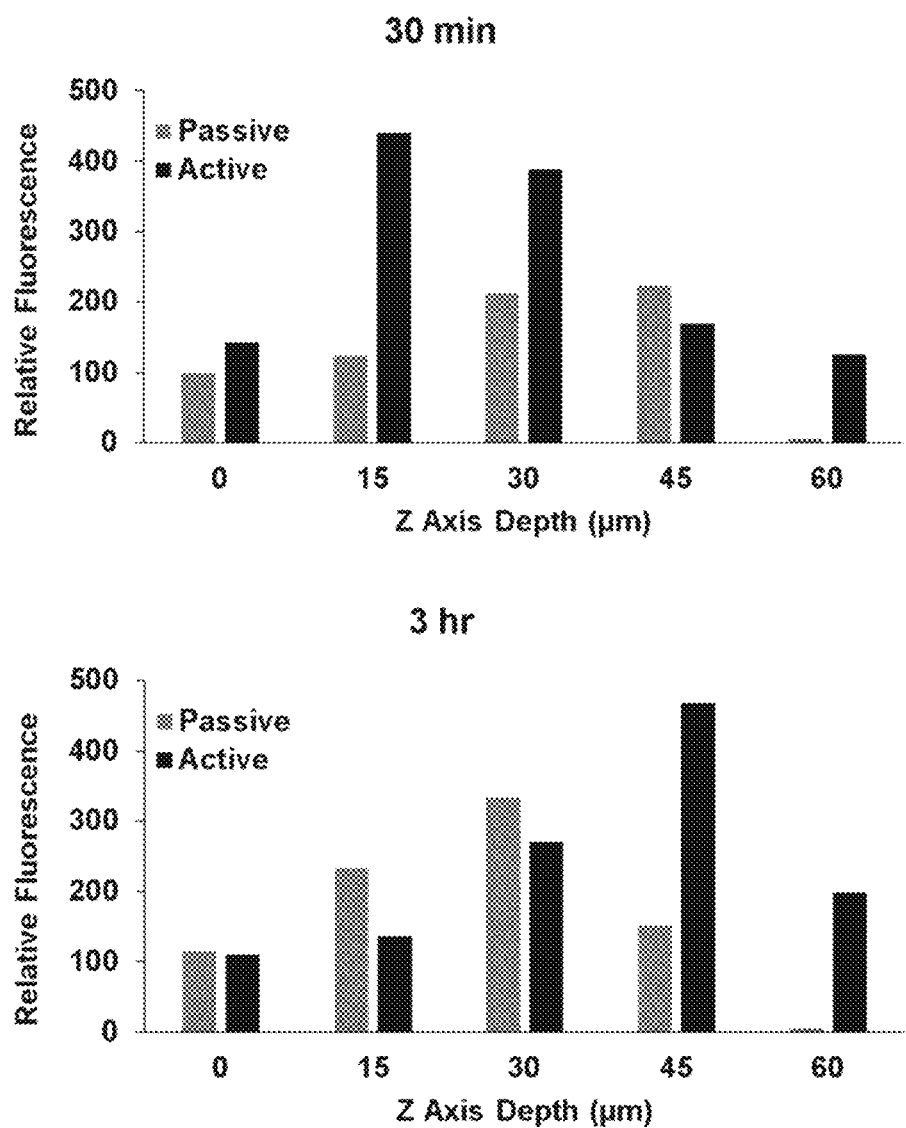
FIG. 13 shows graphs comparing the total fluorescence intensity obtained by measuring the fluorescence intensity on each image of FIG. 12.

Next, the skin tissue of hairless mice was dissected and placed in the upper chamber of a Franz diffusion cell. The inside of the diffusion cell was filled with PBS. The PKH-exosomes were dispersed in PBS at a suitable concentration, for example, a concentration of $1\times10^5$ particles/mL to $1\times10^9$ particles/mL, and then applied to the outer surface of the mouse skin tissue. At this time, nonwoven fabric was pre-placed on the outer surface of the mouse skin tissue in order to prevent drying of the PKH-exosome solution, and the PKH-exosome solution was injected between the nonwoven fabric and the skin tissue. Then, the PKH-exosomes and the skin tissue were allowed to react for 30 minutes to 1 hour. Alternatively, after the PKH-exosome solution was injected between the nonwoven fabric and the skin tissue, a microcurrent was allowed to flow through the skin tissue for a predetermined time, for example, 30 minutes to 1 hour. After completion of the reaction, the PKH-exosomes delivered into the skin tissue were immediately observed with a confocal fluorescence microscope (Leica, SP8X), or the skin tissue and the PKH-exosome solution were additionally allowed to react for 1 to 6 hours, and then the PKH-exosomes were observed with a confocal fluorescence microscope. As a result, it was confirmed that the exosomes of the present invention are able to effectively penetrate through the skin barrier, so that exosomes of the present invention are able to be delivered deep into the skin tissue and effectively absorbed into the skin (FIGS. 12 and 13).

Therefore, a skin external preparation or cosmetic composition containing the exosomes as an active ingredient will effectively act in the prevention, suppression, alleviation, amelioration or treatment of pruritus.

Example 10

Treatment of Human Skin with Composition Containing Exosomes as Active Ingredient A "test product" composed of an ampoule which contains the exosomes obtained according to one embodiment of the present invention (containing a translucent milky liquid composition), a liquid-soaked sheet mask (a white sheet mask soaked with the above translucent milky liquid) and a percutaneous penetration-promoting sheet mask (a silvery sheet mask including an iontophoresis device) was applied once to the face of a person with severe face flushing and skin trouble associated with pruritus (hereinafter, referred to as "case 1"). It was evaluated whether the skin trouble and the face flushing were alleviated or ameliorated. In addition, the test product was applied once to the face of a person with face flushing (hereinafter, referred to as "case 2"). It was evaluated whether the overall skin tone and the face flushing were ameliorated.

Figure 15:
FIG. 15 depicts photographs comparing skin conditions between before and after the treatment of human skin with a test product containing exosomes according to one embodiment of the present invention.

With only single use of the "test product" containing the exosomes of the present invention, the face flushing and skin trouble of "case 1" was remarkably ameliorated (see case 1 of FIG. 15), and the overall skin tone of "case 2" was ameliorated and the face flushing of "case 2" was alleviated (see case 2 of FIG. 15). Thus, a skin external preparation or cosmetic composition containing the exosomes of the present invention as an active ingredient has the effect of preventing, suppressing, alleviating or ameliorating face flushing and skin trouble associated with pruritus.

Figure 16:
FIG. 16 depicts photographs showing that erythema and the like on human skin (affected part) were remarkably ameliorated as a result of applying a composition including exosomes according to one embodiment of the present invention to human skin (affected part) and then performing iontophoresis to allow a microcurrent to flow through human skin (affected part) to which the composition was applied.

In addition, the composition containing the exosomes obtained according to one embodiment of the present invention, that is, a suspension containing the exosomes of the present invention, was applied to the affected parts (hand, neck, arm, etc.) of three severe atopic patients complaining of pruritus, three times a week for 1 to 2 weeks, and then iontophoresis allowing a microcurrent to flow through the composition-applied affected part was performed using an iontophoresis device. As a result, severe pruritus in the patients was remarkably alleviated, and erythema of the patients was also remarkably ameliorated (FIG. 16). In the patients to which the composition containing the exosomes of the present invention was applied, severe pruritus and erythema were alleviated and ameliorated so that the prescription of steroids or anti-histamines for these patients would be stopped.

Thus, a skin external preparation or cosmetic composition containing, as an active ingredient, the exosomes obtained by the isolation method according to one embodiment of the present invention, exhibits the effect of preventing, suppressing, alleviating, ameliorating or treating pruritus, as confirmed through the above-described clinical tests.

Example 11

Preparation of Cosmetic Composition Containing Exosomes of the Present Invention 1704 µg/mL of the exosomes prepared in Example 2 above was mixed with and suspended in the components shown in Table 3 below, thereby preparing a cosmetic composition (lotion). The content of each component is shown in Table 3 below.

TABLE 3

Components and their contents of lotion containing exosomes of the present invention

| Components | Contents (wt %) |
|---|---|
| Exosomes prepared in Example 2 | 1 |
| Glycerin | 7.375 |
| Caprylic/capric triglyceride | 6 |
| Cetyl ethylhexanoate | 5 |
| Propanediol | 5 |
| Phenyl trimethicone | 3.5 |
| Stearic acid | 3 |
| 1,2-hexanediol | 2 |
| Panthenol | 2 |
| Cetearyl olivate | 1.8 |
| Sorbitan olivate | 1.2 |
| Diisostearyl malate | 1 |
| Fructan | 1 |
| Ammonium acryloyldimethyl taurate/VP copolymer | 0.3 |
| Arachidyl alcohol | 0.25 |
| Behenyl alcohol | 0.15 |
| Arachidyl glucoside | 0.1 |
| Hydrogenated lecithin | 0.1 |
| Shea butter | 0.09 |
| Xanthan gum | 0.05 |
| Lavender oil | 0.02 |
| Bergamot oil | 0.02 |
| Ceramide NP | 0.02 |
| Orange peel oil | 0.02 |
| Phytospingosine | 0.015 |
| Palmitoyl tetrapeptide-7 | 0.01 |
| Palmitoyl tripeptide-1 | 0.01 |
| Purified water | Balance |

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for suppressing, alleviating, ameliorating or treating pruritus mediated by thymic stromal lymphopoietin (TSLP) in a subject in need thereof, the method comprising:
administering an effective amount of a composition comprising exosomes as an active ingredient to the subject, said exosomes being derived from adipose-derived stem cells; and
decreasing expression and/or production of TSLP in the subject.

2. The method of claim 1, wherein the exosomes are obtained by performing the steps of: (a) adding trehalose to a conditioned medium of adipose-derived stem cells; (b) filtering the conditioned medium having the trehalose added thereto; (c) isolating exosomes from the filtered conditioned medium by tangential flow filtration (TFF); and (d) adding trehalose to a buffer for diafiltration, and performing diafiltration on the isolated exosomes by the TFF using the buffer having the trehalose added thereto.

3. The method of claim 2, wherein the diafiltration is performed continuously or discontinuously.

4. The method of claim 2, wherein the diafiltration is performed using a buffer having at least 4 times volume of the isolated exosomes.

5. The method of claim 2, wherein the TFF is carried out using a TFF filter having a molecular weight cutoff (MWCO) of 100,000 Da, 300,000 Da, 500,000 Da, or 750,000 Da, or a 0.05 µm filter.

6. The method of claim 2, wherein step (c) further comprises concentrating the isolated exosomes to a volume of 1/100 to 1/25 by the TFF.

7. The method of claim 1, wherein the exosomes decrease expression levels of IL-4, IL-31 and TSLP in skin tissue or skin cells.

8. The method of claim 1, wherein the subject is at least one selected from the group consisting of humans, dogs, cats, rodents, horses, cattle, monkeys and pigs.

9. A method for suppressing, alleviating, ameliorating or treating pruritus mediated by thymic stromal lymphopoietin (TSLP) in a subject in need thereof, the method comprising:
(a) (a1) applying a composition comprising exosomes as an active ingredient to a skin of the subject, said exosomes being derived from adipose-derived stem cells; or (a2) contacting or attaching a patch, a mask pack or a mask sheet, which has the composition applied thereto or soaked therein, to the skin; or (a3) sequentially performing (a1) and (a2); and
(b) decreasing expression and/or production of TSLP in the skin tissue and/or the skin cells of the subject.

10. The method of claim 9, wherein the exosomes are contained in or mixed with at least one of hydrogel, hyaluronic acid, salt of hyaluronic acid, and hyaluronate gel.

11. The method of claim 10, wherein the hydrogel is obtained by dispersing a gelled polymer in a polyhydric alcohol.

12. The method of claim 11, wherein the gelled polymer is at least one selected from the group consisting of pluronic, purified agar, agarose, gellan gum, alginic acid, carrageenan, *cassia* gum, xanthan gum, galactomannan, glucomannan, pectin, cellulose, guar gum, and locust bean gum, and the polyhydric alcohol is at least one selected from the group consisting of ethylene glycol, propylene glycol, 1,3-butylene glycol, isobutylene glycol, dipropylene glycol, sorbitol, xylitol, and glycerin.

13. The method of claim 9, wherein the composition is used in at least one form selected from the group consisting of patches, mask packs, mask sheets, creams, tonics, ointments, suspensions, emulsions, pastes, lotions, gels, oils, packs, sprays, aerosols, mists, foundations, powders, and oilpapers.

14. The method of claim 13, wherein the composition is applied to or soaked in at least one surface of the patch, mask pack or mask sheet.

15. The method of claim 9, further comprising (c) performing iontophoresis by allowing a microcurrent to flow through the skin having the composition applied thereto.

16. The method of claim 15, further comprising contacting or attaching an iontophoresis device to the skin.

17. The method of claim 16, wherein the iontophoresis device comprises at least one battery selected from the group consisting of flexible batteries, lithium-ion secondary batteries, alkaline batteries, dry cells, mercury batteries, lithium batteries, nickel-cadmium batteries, and reverse electrodialysis batteries, or comprises a patch, a mask pack or a mask sheet provided with the at least one battery.

18. The method of claim 9, wherein the subject is at least one selected from the group consisting of humans, dogs, cats, rodents, horses, cattle, monkeys and pigs.

\* \* \* \* \*